(12) United States Patent
Smith

(10) Patent No.: US 8,389,223 B2
(45) Date of Patent: Mar. 5, 2013

(54) PROBES FOR ANIONIC CELL SURFACE DETECTION

(75) Inventor: Bradley D. Smith, Granger, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 41 days.

(21) Appl. No.: 12/874,689

(22) Filed: Sep. 2, 2010

(65) Prior Publication Data

US 2010/0331542 A1 Dec. 30, 2010

Related U.S. Application Data

(62) Division of application No. 11/749,474, filed on May 16, 2007, now abandoned.

(60) Provisional application No. 60/802,116, filed on May 22, 2006.

(51) Int. Cl.
*G01N 33/53* (2006.01)
*C07F 15/04* (2006.01)

(52) U.S. Cl. .......... 435/7.1; 435/7.21; 435/7.23; 546/12

(58) Field of Classification Search .................. 435/7.1, 435/7.21, 7.23; 546/12
See application file for complete search history.

(56) References Cited

U.S. PATENT DOCUMENTS

| | | | |
|---|---|---|---|
| 4,910,152 A | 3/1990 | Meyers et al. | |
| 6,229,024 B1 | 5/2001 | Schmued | |
| 2002/0009762 A1 | 1/2002 | Flint et al. | |
| 2003/0100520 A1 | 5/2003 | Needleman et al. | |
| 2006/0134001 A1* | 6/2006 | Frangioni | 424/9.6 |
| 2006/0216775 A1 | 9/2006 | Burkart et al. | |
| 2010/0029494 A1 | 2/2010 | Cherkasov et al. | |

OTHER PUBLICATIONS

Zaheer et al. Molecular Imaging (2002) 1(4): 354-364.*
Leevy et al. J. Am. Chem. Soc.( 2006; published on-line Dec. 8, 2006) 128: 16476-16477.*
Jonathan F. Tait et al., "Measurement of the affinity and cooperativity of annexin V-membrane binding under conditions of low membrane occupancy," Analytical Biochemistry 329 (2004) 112-119.
S.-B. Ning et al., "Apoptotic Cell Death and Cellular Surface Negative Charge Increase in Maize Roots Exposed to Cytotoxic Stresses," Annals of Botany 87: 575-583, 2001.
Jeanne Dachary-Prigent et al., "Calcium Involvement in Aminophospholipid Exposure and and Microparticle Formation during Platelet Activation: A Study Using Ca2+-ATPase Inhibitors," Biochemistry 1995, 34, 11625-11634.
Dietrun Kamp et al., "Inhibition and Stimulation of Phospholipid Scrambling Activity. Consequences for Lipid Asymmetry, Echinocytosis, and Microvesiculation of Erythrocytes," Biochemistry 2001, 40, 9438-9446.
Georjeana A. Wurth et al., "Evidence that cytosolic calcium increases are not sufficient to stimulate phospholipid scrambling in human T-lymphocytes," Biochem. J. (2002) 362, 701-708.

Claudette Pelassy et al., "Regulation of Phosphatidylserine Exposure at the Cell Surface by the Serine-Base Exchange Enzyme System during CD95-Induced Apoptosis," Biochemical Pharmacology, vol. 59, pp. 855-863, 2000.
AV Koulov et al., "Detection of apoptotic cells using a synthetic fluorescent sensor for membrane surfaces that contain phosphatidylserine," Cell Death and Differentiation (2003) 10, 1357-1359.
RA Schlegel et al., "Phosphatidylserine, a death knell," Cell Death and Differentiation (2001) 8, 551-563.
Eyk A. Schellenberger et al., "Surface-Functionalized Nanoparticle Library Yields Probes for Apoptotic Cells," ChemBioChem 2004, 5, 275-279.
Annette M. Koch et al., "Transport of Surface-Modified Nanoparticles Through Cell Monolayers," ChemBioChem 2005, 6, 337-345.
Manon Van Engeland et al., "Annexin V-Affinity Assay: A Review on an Apoptosis Detection System Based on Phosphatidylserine Exposure," Cytometry 31:1-9 (1998).
Robert A. Schwartzman et al., "Apoptosis: The Biochemistry and Molecular Biology of Programmed Cell Death," Endocrine Reviews, vol. 14, No. 2, 1993.
David Arboledas et al., "Role of the N-terminus in the structure and stability of chicken annexin V," FEBS Letters 416 (1997) 217-220.
Tatsuya Matsura et al., "Phosphatidylserine peroxidation/externalization during staurosporine-induced apoptosis in HL-60 cells," FEBS Letters 524 (2002) 25-30.
Atanas V. Koulov et al., "Biophysical Studies of a Synthetic Mimic of the Apoptosis-Detecting Protein Annexin V," Israel Journal of Chemistry, vol. 45, 2005, pp. 373-379.
J. Jack Li et al., "Large-Scale Synthesis of Nearly Monodisperse CdSe/CdS Core/Shell Nanocrystals Using Air-Stable Reagents via Successive Ion Layer Adsorption and Reaction," J. Am. Chem. Soc. 2003, 125, 12567-12575.
B. Plasier et al., "Automatic image analysis for quantification of apoptosis in animal cell culture by annexin-V affinity assay," Journal of Immunological Methods 229 (1999) 81-95.
Tonya Laakko et al., "Versatility of merocyanine 540 for the flow cytometric detection of apoptosis in human and murine cells," Journal of Immunological Methods 261 (2002) 129-139.
Scott D. Bunge et al., "Growth and morphology of cadmium chalcogenides: the synthesis of nanorods, tetrapods, and spheres from CdO and Cd(O2CCH3)2" J. Mater. Chem., 2003, 13, 1705-1709.
Tarik Z. Belhocine et al., "Nuclear Medicine in the Era of Genomics and Proteomics: Lessons from Annexin V," Journal of Proteome Research 2004, 3, 345-349.

(Continued)

*Primary Examiner* — Susan Hanley
(74) *Attorney, Agent, or Firm* — Schwabe, Williamson & Wyatt

(57) ABSTRACT

Embodiments of the present invention are generally directed to compositions comprising a class of molecular probes for detecting the presence of anionic cell surfaces. Embodiments include compositions that are enriched for these compositions and preparations, particularly preparations suitable for use as laboratory/clinical reagents and diagnostic indicators, either alone or as part of a kit. An embodiment of the invention provides for a highly selective agent useful in the discernment and identification of dead or dying cells, such as apoptotic cells, in a relatively calcium-free environment. An embodiment of the invention provides a selective agent for the identification of bacteria in a mixed population of bacterial cells and nonbacterial cells.

2 Claims, 12 Drawing Sheets

OTHER PUBLICATIONS

J. Middleton Boon et al., "Chemical Control of Phospholipid Distribution Across Bilayer Membranes," Medicinal Research Reviews, vol. 22, No. 3, 251-281, 2002.

Junor A. Barnes et al., "Proteolytic signals in the primary structure of annexins," Molecular and Cellular Biochemistry 231: 1-7, 2002.

LD Tomei et al., "Apoptosis in C3H/10T1/2 Mouse Embryonic Cells: Evidence for Internucleosomal DNA Modification in the Absence of Double-Strand Cleavage," PNAS 1993; 90; 853-857.

David A. Bird et al., "Receptors for oxidized low-density lipoprotein on elicited mouse peritoneal macrophages can recognize both the modified lipid moieties and the modified protein moieties: Implications with respect to macrophage recognition of apoptotic cells," PNAS 1999; 96; 6347-6352.

Benoit Dubertret et al., "In Vivo Imaging of Quantum Dots Encapsulated in Phospholipid Micelles," Science, vol. 298, Nov. 29, 2002.

X. Michalet et al., "Quantum Dots for Live Cells, in Vivo Imaging, and Diagnostics," Science, vol. 307, Jan. 28, 2005.

C. Lakshmi et al., "Fluorophore-linked zinc(II)dipicolylamine coordination complexes as sensors for phosphatidylserine-containing membranes," Tetrahedron 60 (2004) 11307-11315.

Roger Hanshaw et al., "Fluorescent Detection of Apoptotic Cells by Using Zinc Coordination Complexes with a Selective Affinity for Membrane Surfaces Enriched with Phosphatidylserine," ChemBioChem 2005, 6, pp. 2214-2220.

Bentz, Joe et al., "La3+—Induced Fusion of Phosphatidylserine Liposomes," Biophysical Journal, Apr. 1988, vol. 53, pp. 593-607.

Farge, Emmanuel, et al., "Enhancement of Endocytosis due to Aminophospholipid Transport Across the Plasma Membrane of Living Cells," Am J Physiol Cell Physiol, 1999, vol. 276, pp. C725-C733.

Giaimis, Jean et al., "Flow Cytometry Distinction Between Adherent and Phagocytized Yeast Particles," Cytometry, 1994, vol. 17, pp. 173-178.

Gorbenko, Galyna P. et al., "Binding of Lysozyme to Phospholipid Bilayers: Evidence for Protein Aggregation upon Membrane Association," Biophysical Journal, Jul. 2007, vol. 93, pp. 140-153.

Gottlieb, Roberta A. et al., "Apoptosis Induced in Jurkat Cells by Several Agents is Preceded by Intracellular Acidification," Proc., National Acad. Sci., USA, Jan. 1996, vol. 93, pp. 654-658.

Kakio, Atsuko et al., "Formation of a Membrane-Active Form of Amyloid Beta-Protein in Raft-like Model Membranes," Biochemical and Biophysical Research Communications, 2003, vol. 303, pp. 514-518.

Kinraide, Thomas B., "Use of a Gouy-Chapman-Stern Model for Membrane-Surface Electrical Potential to Interpret Some Features of Mineral Rhizotoxicity," Plant Physiol. 1994, vol. 106, pp. 1583-1592.

Lagadic-Gossmann, D. et al., "Alterations of Intracellular pH Homeostasis in Apoptosis: Origins and Roles," Cell Death and Differentation, 2004, vol. 11, pp. 953-961.

Lakowicz, Joseph R. et al., "Release of the Self-Quenching of Fluorescence Near Silver Metallic Surfaces," Analytical Biochemistry, 2003, vol. 320, pp. 13-20.

Linnertz, Holger et al., "Microenvironment of the High Affinity ATP-Binding Site of Na+/K+-ATPase is Slightly Acidic," Biochemical and Biophysical Research Communications, 1999, vol. 254, pp. 215-221.

McLaughlin, Stuart et al., "Adsorption of Divalent Cations to Bilayer Membranes Containing Phosphatidylserine," Journal of Gen. Physiol. Apr., 1981, vol. 77, pp. 445-473.

McLaughlin, Alan C, "Phosphorus-31 and Carbon-13 Nuclear Magnetic Resonance Studies of Divalent Cation Binding to Phosphatidylserine Membranes: Use of Cobalt as a Paramagnetic Probe," Biochemistry, 1982, vol. 21, pp. 4879-4885.

Puskin, Jerome S. et al., "Na+ and H-Dependent Mn2+ Binding to Phosphatidylserine Vesicles as a Test of the Gouy-Chapman-Stern Theory," J. Membrane Biol, 1980, vol. 52, pp. 69-94.

Takemoto, Kazuhisa et al., A Fluorescence Dequenching Method for Monitoring Exocytotic Membrane Fusion in Fertilization of Single Sea Urchin Eggs, Biology of the Cell, 1999, vol. 91, pp. 5-15.

Tatulian, Suren A., "Evaluation of Divalent Cation Binding to Phosphatidylserine Membranes by an Analysis of Concentration Dependence of Surface Potential," Journal of Colloid and Interface Science, 1995, vol. 175, pp. 131-137.

Yi, Dandan et al., "Interaction of Arginine Oligomer with Model Membrane," Biochemical and Biophysical Research Communications, 2007, vol. 359, pp. 1024-1029.

Barton, Peter G, "The Influence of surface Charge Density of Phosphatides on the Binding of Some Cations," The Journal of Biological Chemistry, 1968, vol. 243, No. 14, pp. 3884-3890.

Brown, R. Stephen, "Self-Quenching of Nitrobenzoxadiazole Lagbeled Phospholipids in Lipid Membranes," Journal of Chemical Physics, 1994, vol. 100, No. 8, pp. 6019-6027.

Shrive, Jason D. A. et al., "Influence of Structural Heterogeneity on the Fluorimetric Response Characteristics of Lipid Membranes Containing Nitrobenzoxadiazolyldipalmitoylphosphatidylethanolamine," Langmuir, 1996, vol. 12, pp. 4921-4928.

Burdette, Shawn C. et al., "Fluorescent Sensors fo Zn2+ Based on a Fluorescein Platform: Synthesis, Properties and Intracellular Distribution," Journal of the American Chemical Society, 2001, vol. 123, pp. 7831-7841.

Vermes et al., "A Novel Assay for Apoptosis Flow Cytometric Detection of Phosphatidylserine Expression on Early Apoptotic Cells Using Fluorescein Labelled Annexin V," J. Immunol. Methods (1995) 184: pp. 39-51.

Ishii et al., "Distinct Localization of Lipid Rafts and Externalized Phosphatidylserine at the Surface of Apoptotic Cells," Biochem. Biophys. Res. Comm. (Feb. 2005) 327: pp. 94-99.

* cited by examiner

SCHEME 1

SCHEME 2

SCHEME 3

US 8,389,223 B2

PROBES FOR ANIONIC CELL SURFACE DETECTION

CROSS REFERENCE TO RELATED APPLICATIONS

The present application is a divisional application of U.S. patent application Ser. No. 11/749,474, filed May 16, 2007, now abandoned, entitled "Probes for Anionic Cell Surface Detection," which claims priority to U.S. Provisional Patent Application No. 60/802,116, filed May 22, 2006, entitled "Phosphatidylserine Sensors and Uses Thereof in Cell Apoptosis," the entire disclosures of which are hereby incorporated by reference in their entirety.

GOVERNMENT INTEREST STATEMENT

The United States Government owns rights in the present invention as research relevant to the development of the invention was supported by United States federal funds from the National Institutes of Health, Grant Number RO1 GM 059078 and from the United States Department of Energy's National Nuclear Security Administration contract DE-AC04-94AL8500.

TECHNICAL FIELD

Embodiments of the present invention relate generally to probes for anionic cell surface detection, such as bacterial cell surface sensing molecules or phosphatidylserine sensing molecules, particularly detecting molecules that are fluorescein derivatives, such as PSS480, or that possess other reporter elements, such as cyanine dye, biotin or a quantum dot (QD). The present invention also relates to methods of using these molecules in various clinical and pharmaceutical treatment and screening/selection protocols, such as in the sensing, detection, identification, and/or treatment of animal cell death, a cell process that is known to raise the amounts of anionic phosphatidylserine on the cell surface, or bacteria which have anionic cell surfaces.

BACKGROUND

The phospholipid bilayer surrounding animal cells is a dynamic environment made up of four principle phospholipid components, phosphatidylcholine (PC), phosphatidylethanolamine (PE), phosphatidylserine (PS), and sphingomyelin (SM). These four phospholipids are distributed between two monolayers of the membrane in an asymmetrical fashion, with the choline-containing lipids, PC and SM, largely populating the external leaflet, while the aminophospholipids, PE and especially PS, are restricted primarily to the inner membrane leaflet. This membrane asymmetry has been known for some time, and there is a consensus that it is maintained by the concerted action of a family of translocase enzymes. Efforts to elucidate the structure and mechanism of these transport proteins are ongoing and are described elsewhere.

Apoptosis, or the sequence of events collectively known as "programmed cell death," is an important process whereby cells are intentionally marked for clearance from the body. Apoptosis is a central process in developmental biology and also in many types of diseases. For example, selective induction of apoptosis in cancerous tissue is an attractive chemotherapeutic strategy, and detection of apoptosis is therefore a key step in the drug development process. Various strategies for detecting apoptosis have been reported, including monitoring of intracellular caspase activity, observing nucleic acid fragmentation, and detection of membrane permeabilization. These assays are employed as diagnostic tools for identifying apoptosis, but each has limitations that render it imperfect in certain situations.

Loss of the phospholipid asymmetry inherent to healthy animal cell membranes is a hallmark of apoptosis, regardless of the initiating stimulus. During the early to middle stages of apoptosis, the PS normally found exclusively on the inner membrane monolayer becomes scrambled between the two membrane leaflets. PS is the most abundant anionic phospholipid component in the plasma membrane of most animal cells, and PS externalization is a contributing factor to the recognition of dead and dying cells by macrophages. The externalized PS can be detected on the cell surface using indicator-labeled reagents that preferentially bind the PS headgroup. PS externalization precedes the upregulation of protease activity in the cytosol, and occurs before membrane permeabilization begins. Another attractive feature of this cell surface assay is that it avoids the complications of other assays that require access to the cytosol. Furthermore, there is evidence that PS exposure on the cell surface is a common final outcome for other death processes such as senescence, mitotic catastrophe and autophagy, etc. Thus, the strategy of PS recognition makes it possible to consider applications for site-specific in vivo imaging of dead and dying tissue that would be useful in the treatment of various diseases such as cancer and cardiovascular disease.

The annexins are a group of proteins that bind anionic phospholipids in a $Ca^{2+}$-dependent manner. One member of the family, Annexin V (Anx V), binds PS with high selectivity and high affinity in the presence of $Ca^{2+}$, making it well suited for detection of apoptosis. A variety of fluorophore-labeled versions of Anx V are commercially available, and detection of cell-surface PS by this technique has become a standard protocol in cell biology research.

Even though Anx V derivatives are widely used for PS-sensing applications and apoptosis detection, Anx V has several disadvantages and limitations. For instance, the unfunctionalized Anx V protein has a mass of about 36 KDa, which restricts its use to those applications where a PS sensor of this size can be accommodated. Furthermore, Anx V-PS binding requires millimolar levels of $Ca^{2+}$ in order to produce the nanomolar dissociation constants that make using the protein desirable. This level of $Ca^{2+}$ may be problematic in situations where other processes may need to be monitored simultaneously. Additionally, animal cells frequently have integral membrane phospholipid transport proteins, called "scramblases," that can move phospholipids nonspecifically between the two membrane monolayers. These scramblases are activated by micromolar $Ca^{2+}$ levels, well below that necessary for Anx V-PS binding. Thus, false positives may occur when using Anx V to detect apoptosis. The rate of Anx V-PS binding is also quite slow. Complete membrane binding by Anx V-PS often requires incubation periods of up to one hour, which is problematic for many types of kinetic assays: Anx V is also susceptible to N-terminal proteolytic degradation. In addition, annexin V is a protein that may not have the necessary chemical stability for employment in high-throughput screening of cancer drugs, and may lack the biochemical stability necessary for in vivo imaging of dying tissue.

Another report provided an anthracene-derivated DPA zinc complex for sensing apoptotic cells. However, anthracene is often not an ideal probe in imaging studies because of the short emission wavelength and photobleaching.

These and other limitations demonstrate that a need continues to exist in the art for alternative molecular probes that may be substituted for annexin V, that will bind PS-rich membranes in a Ca2+-independent manner. These kinds of molecules would be extremely useful in further characterizing, detecting, monitoring and/or screening for cell apoptosis and other clinical conditions associated with a relative increase and/or presence of PS.

In addition, the anionic surface of bacterial cells provides an environment that is analogous in certain characteristics with apoptotic cells. In particular, the surfaces of bacterial cells are anionic and thus probes targeting anionic cell surfaces may be used to identify the presence of bacteria. Thus, a suitable molecular probe or group of probes may be capable both of detecting the presence of apoptotic cells and the presence of bacterial cells.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the figures of the accompanying drawings.

FIG. 7A presents Scheme 1 illustrating a three-modular three component design that contains a PS affinity group (two $Zn^{2+}$-DPA) subunits that are oriented meta on a phenyl ring that is attached via a (tris)ethyleneoxy linker to a reporter element. FIG. 7B presents Scheme 2 showing a three-modular design that incorporates practical reporter elements. In Scheme 2, the utility of the fluorescence derivative PSS-480 was demonstrated in fluorescence microscopy and flow cytometry studies. A PSS-Biotin complex, a biotinylated version that may be visualized using indicator-labeled streptavidin, including streptavidin-conjugated quantum dots is also illustrated. FIG. 7C presents Scheme 3 illustrating a CdSe/CdS quantum dot system (PSS-Green QD) coated with the PS affinity group.

FIG. 8B shows fluorescence of cells stained with PSS-480. FIG. 8C shows a phase contrast image of treated cells. FIG. 8D shows an overlay of both FIG. 8A and FIG. 8B onto a phase contrast image.

FIG. 9B shows fluorescence of cells stained with PSS-480. FIG. 9C shows a phase contrast image of treated cells. FIG. 9D shows an overlay of both FIG. 9A and FIG. 9B onto a phase contrast image.

FIGS. 11A and 11B present phase contrast and fluorescence images (11A and 11B, respectively) of a field of Jurkat cells treated with 10 μM PSS-480 at 0° C. FIGS. 11C and 11D present phase contrast and fluorescence images (11C and 11D, respectively) of a field of Jurkat cells treated with 10 μM PSS-480 at 37° C. Apoptosis was induced by treatment with camptothecin (10 μM) for 3.5 h prior to staining (60× magnification).

DETAILED DESCRIPTION OF EMBODIMENTS OF THE INVENTION

Figure 1:
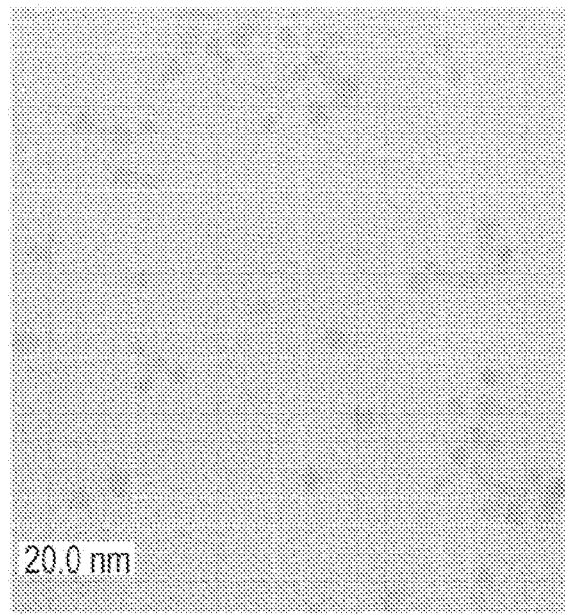
FIG. 1 presents a transmission electron micrograph of CdSe/CdS nanoparticles used to prepare a PSS Green QD. The sample was prepared by allowing a solution of nanoparticles in $CHCl_3$ to evaporate on a copper-coated TEM grid. The particles exhibit a roughly spherical geometry of 4-5 nm in diameter.
Figure 2A:
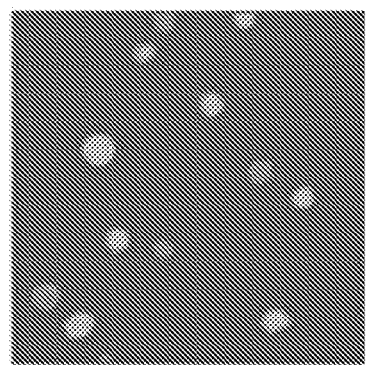
FIGS. 2A-2D present fluorescence micrographs (40× magnification) of Jurkat cells treated with camptothecin (10 μM) for 3.5 h to induce apoptosis, then stained with PSS-480 (5 μW) and 7-amino-acitomycin-D (7AAD) (500 ng $mL^{-1}$). 2A) Fluorescence of cells stained with PSS-480; 2B) fluorescence of cells stained with 7AAD; and 2C) an overlay of (2A and 2B). Those cells stained only with PSS-480 are apoptotic, as illustrated by exclusion of 7AAD. The apoptotic cells are indicated with circles. 2D) A phase-contrast image of all cells in the field. No staining of healthy cells with PSS-480 was observed in the absence of treatment with camptothecin.
Figure 2B:
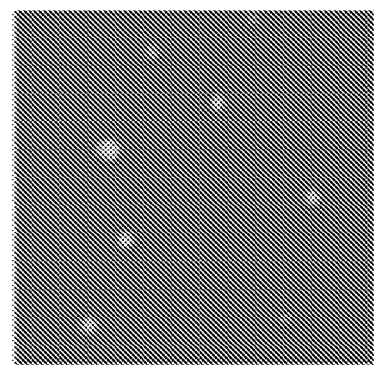
Figure 2C:
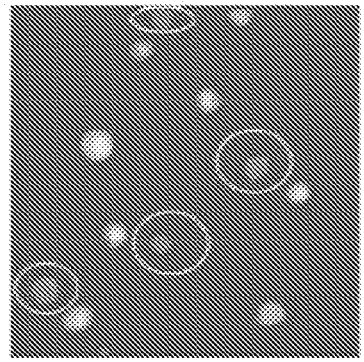
Figure 2D:
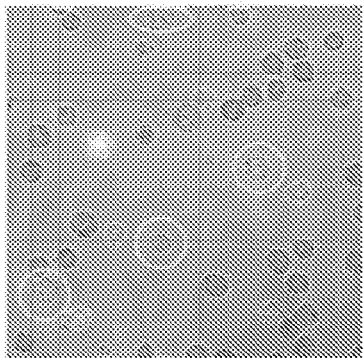
Figure 3A:
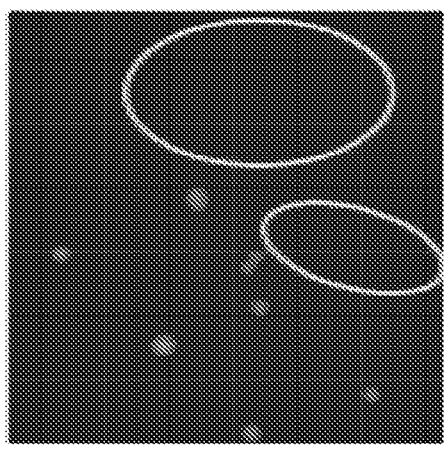
FIGS. 3A-3D present fluorescence micrographs (40× magnification) of Jurkat cells treated with 10 μM camptothecin for 3.5 h and stained with 7AAD (500 ng $mL^{-1}$), annexin V-FITC, and PSS-biotin (100 μM) with a blue-emitting streptavidin-dye conjugate (400 nM). All reagents were added simultaneously. Cells were then incubated for 15 minutes at 37° C. 2A) Cells stained with the nuclear stain 7AAD; 2B) cells stained with annexin V-FITC; 2C) cells stained with PSS-biotin/streptovidin Marina Blue conjugate (460 nm emission); and 2D) bright-field image of the entire field of cells. Cells in the circled regions of each image are apoptotic. No staining of healthy cells was observed in the absence of treatment with camptothecin.
Figure 3B:
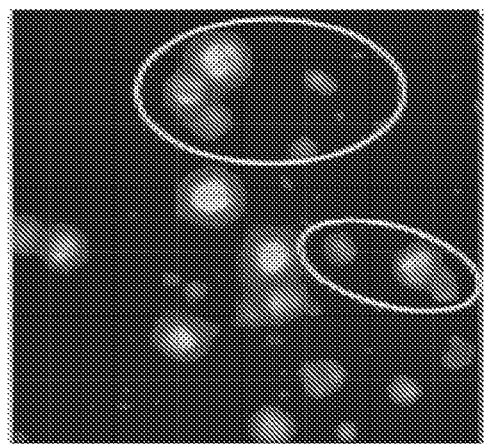
Figure 3C:
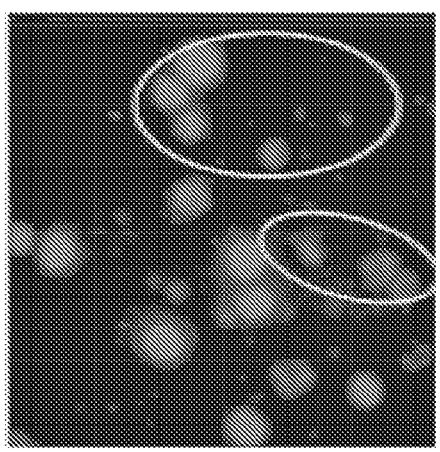
Figure 3D:
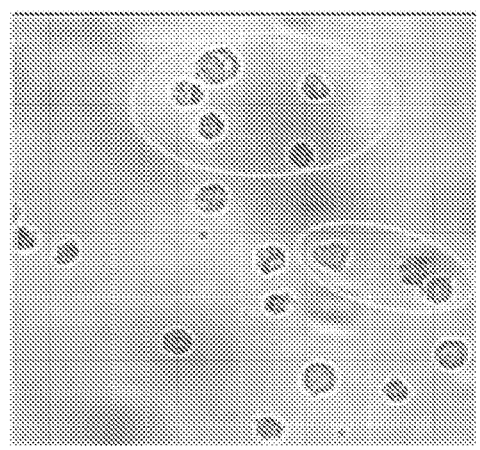

In the following detailed description, reference is made to the accompanying drawings which form a part hereof, and in which are shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

For the purposes of the description, a phrase in the form "A/B" means A or B. For the purposes of the description, a phrase in the form "A and/or B" means "(A), (B), or (A and B)". For the purposes of the description, a phrase in the form "at least one of A, B, and C" means "(A), (B), (C), (A and B), (A and C), (B and C), or (A, B and C)". For the purposes of the description, a phrase in the form "(A)B" means "(B) or (AB)" that is, A is an optional element.

The description may use the phrases "in an embodiment," or, "in embodiments," which may each refer to one or more of the same or different embodiments. Furthermore, the terms "comprising," "including," "having," and the like, as used with respect to embodiments of the present invention, are synonymous.

As used in the description of the present invention, the term "a", "an" and "the" include reference to the plural unless the context as herein presented clearly indicates otherwise.

As used in the description of the present invention, the term "about" is defined as an amount that is more or less than 5%, or even 15% of the stated value. For example, a concentration of "about" 50 µM" would include a range of from 2.5 µM to 7.5 µM above and below the value of 50 µM ("about 50 µM would, for example, be defined to include a concentration range of at least from 42.5 µM to 57.5 µM).

As used in the description of the present invention, the terms "apoptotic," "dying" or "dead" are defined as conditions of a cell or a tissue containing cells that have an enhanced concentration of phosphatidylserine exposed on the cell surface of the cell.

As used in the description of the present invention, the term "calcium-free" is defined as a concentration of calcium that is less than that amount of calcium that is present in a standard cellular system required for the binding of a non-phosphatidylserine-sensitive (PSS)-based detection molecule, such as annexin, to the surface of a cell. In some embodiments, "calcium free" is defined as a concentration of calcium that is equal to or less than about 200 µM, about 100 µM, about 50 µM, about 20 µM or less. In some embodiments, essentially "calcium-free" is defined as about 100 µM Ca$^{2+}$ or less.

As used in the description of the present invention, the term "Kd" is defined as a dissociation constant for phosphatidylserine.

As used in the description of the present invention, the term "<Kd" is defined as a calculated dissociation constant for phosphatidylserine expressed as a Kd value that is a Kd<10$^{-6}$, 10$^{-5}$, 10$^{-4}$, 10$^{-3}$, or even 10$^{-2}$, or less. The term "weaker Kd" is used to define a Kd that is numerically greater. For example, the Kd for the membrane of a healthy animal cell is weaker than the Kd for an apoptotic membrane that is relatively enriched in phosphatidylserine, so the numerical value of Kd for the membrane of a healthy animal cell is higher than the numerical value of Kd for an apoptotic membrane that is relatively enriched in phosphatidylserine.

Embodiments of the present invention are generally directed to compositions comprising a class of molecular probes for detecting the presence of anionic cell surfaces. Embodiments include compositions that are enriched for these compositions and preparations, particularly preparations suitable for use as laboratory/clinical reagents and diagnostic indicators, either alone or as part of a kit. An embodiment of the invention provides for a highly selective agent useful in the discernment and identification of dead or dying cells, such as apoptotic cells, in a relatively calcium-free environment. An embodiment of the invention provides a selective agent for the identification of bacteria in a mixed population of bacterial cells and nonbacterial cells.

In embodiments of the invention, a molecular probe is provided having an affinity group coupled via a linker to a reporter element. In an embodiment a suitable affinity group comprises zinc(II) dipicolylamine (ZN-DPA) coordination complexes, with such an affinity group having the following structure:

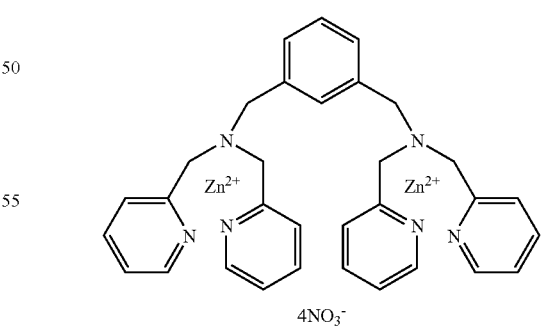

In an embodiment, there is provided a construct for detecting the presence of an anionic cell surface element, comprising the following structure:

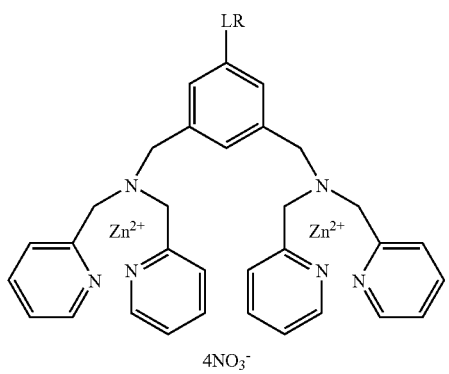

wherein L is a linker, and R is a reporter element.

For the purposes of describing embodiments of the present invention, the term construct generally refers to a compound having multiple components, for example an affinity group, linker, and reporter element. The term construct includes the use of various reporter elements whether fluorescein, cyanine dyes, biotin, or derivatives thereof, or a quantum dot, etc.

In addition to its role of connecting the affinity group to the reporter element, the linker also affects the lipophilicity of the probe molecule and thus modulates the affinity and selectivity of the cell recognition process. The linker also affects the pharmacokinetics for in vivo imaging applications. In addition to hydrocarbons, the linker may include heteroatoms such as oxygen, nitrogen, sulfur, phosphorous, etc, that alter the polarity and lipophilicity, and it may also contain functional groups that alter the rigidity such as olefin, aryl, carbonyl, amide, triazole, etc. In an embodiment, a linker may include an ethyleneoxy linker, such as a (tris)ethyleneoxy linker, a pentyl linker, a butyl linker, a glycol linker, or other suitable linkers.

In an embodiment, a reporter element may be a fluorescent molecule or a dye, such as fluorescein or a fluorescein derivative, cyanine dye, biotin or a biotin derivative, an MRI-contrast agent, a radioactive agent, a quantum dot, etc.

In an embodiment, a suitable reporter element may having the following structure:

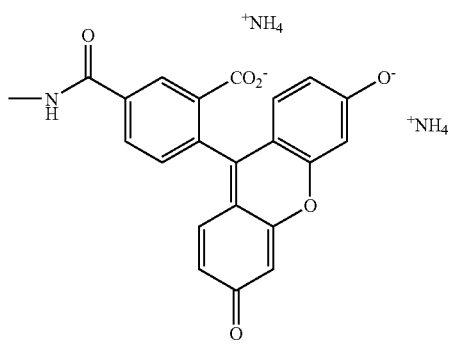

In an embodiment, a suitable reporter element may having the following structure:

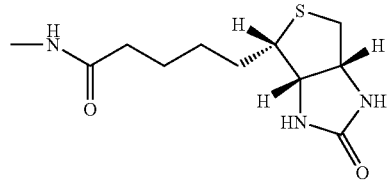 [SMILES: CNC(=O)CCCC[C@@H]1SC[C@@H]2NC(=O)N[C@@H]21]

In an embodiment, a suitable affinity group and linker may be reacted with a quantum dot to allow the quantum dot to serve as the reporter element. In an embodiment, a plurality of affinity group/linker constructs may be reacted with a quantum dot to provide a quantum dot that is partially or substantially surrounded by affinity groups. An exemplary quantum dot in accordance with an embodiment is a CdSe/CdS core/shell nanocrystal.

In an embodiment, a suitable reporter element may have the following structure:

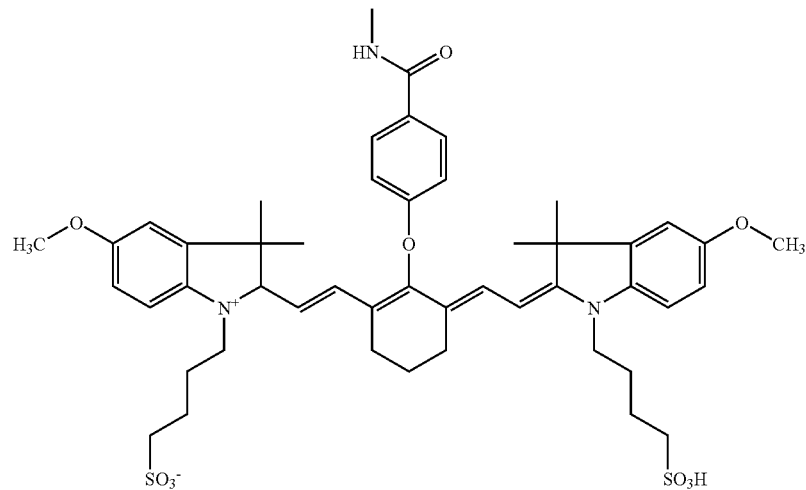

An embodiment of the present invention, in one aspect, presents a novel class of PS sensing molecules that possess a relatively $Ca^{2+}$-independent mechanism. For example, in some embodiments, the relatively $Ca^{2+}$-independent mechanism of phosphatidylserine binding is described as an affinity for binding phosphatidylserine under essentially calcium-free conditions. In some embodiments, essentially calcium-free conditions are described as the presence of calcium at a concentration of 500 μM, 200 μM or 100 μM or less, or even 50 μM or less; or within a range of about 50 μM to about 200 μM.

The dissociation constant of the PS sensing molecules of the invention, in some embodiments, may be described by reference to the Kd of the molecule for phosphatidylserine. In some embodiments, this Kd is described as $10^{-6}$ M or less, $10^{-5}$ M, $10^{-4}$ M or less, such as $10^{-2}$ M, or a Kd in a range of from about $10^{-2}$ M to about $10^{-6}$ M, under essentially calcium-free conditions.

The mechanism of action of the above-mentioned molecular probes is due in part to the affinity of a portion of the compound (affinity group) with the anionic, more specifically, in certain embodiments, monoanionic, surface elements, such as phosphatidylserine in apoptotic cells.

In an embodiment, the probes defined herein may behave as stains, and thus to provide a desirable imaging outcome, a wash step may be utilized after binding/reaction to remove excess probes.

In some embodiments, the PS sensing molecule is a dye. In specific embodiments, the molecule is further described as a fluorescein derivative, such as PSS-480 (Phosphatidylserine Sensor-480 nm excitation). PSS-480 is so named because it is a molecule capable of sensing or detecting the presence of phosphatidylserine (PS), particularly the phosphatidylserine present on the surface of a cell, and possesses the characteristic of absorbing light at a wavelength of about 480 and emitting the light at a higher wavelength.

In an embodiment, there is provided a method of in vivo imaging of apoptotic tissue, chemical regulation of cell cycle progression, and the development of individualized treatment strategies for various types of illness, such as cancer. In some embodiments, imaging is accomplished using the herein described fluorescein derivative, PSS-480.

In embodiments, heptamethine cyanine dyes (C7) with sulfonates are provided. Such compounds have good solubility in water. Such compounds are also beneficial in that the emission of such a near infrared (NIR) dye close to 700-900 nm allows the light to penetrate deeply into tissues. NIR dyes also possess less autofluorescence in this region.

In embodiments, compounds PSS-794 (left, shown below) and PSS-794-TEG (right, shown below) both use a C7 dye as reporter element, and include the Zn-DPA moieties of the affinity group for anionic binding.

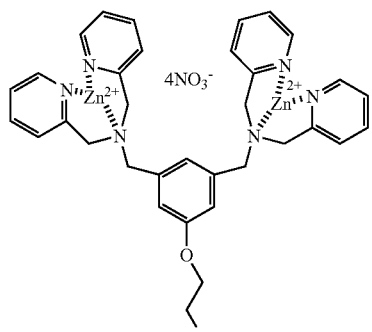

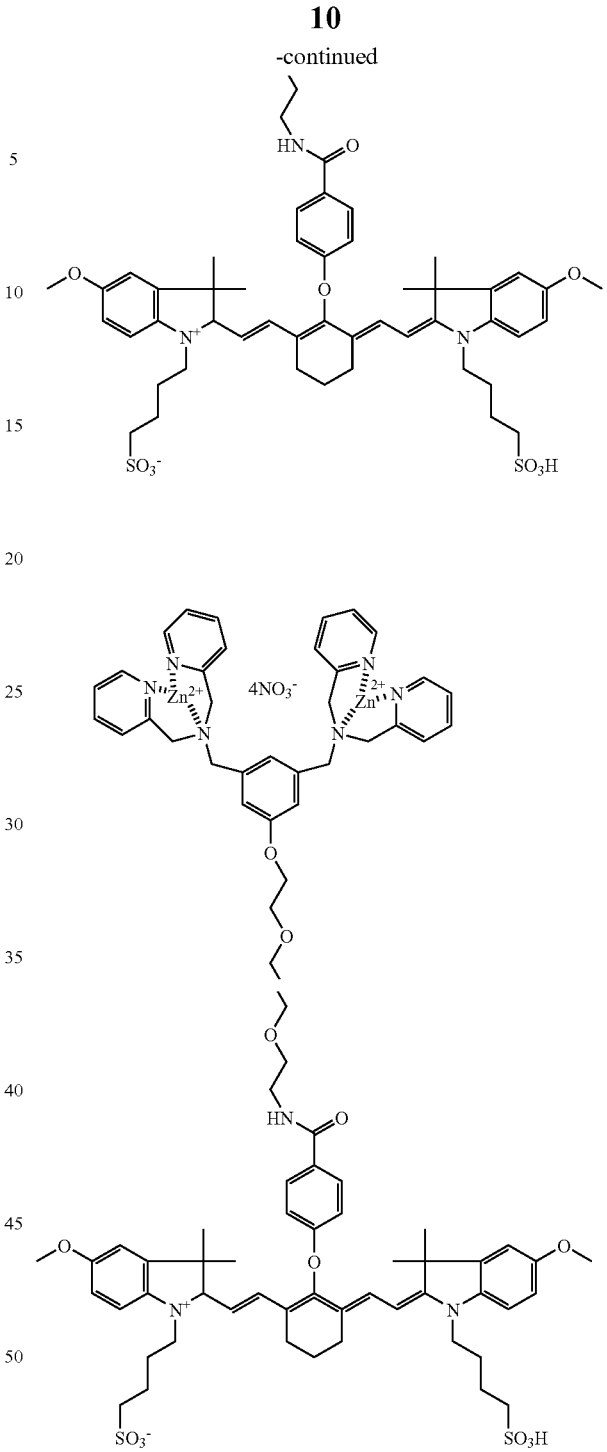

The difference between the compounds is the linker that links the affinity group and the reporter. Due to the glycol linker, PSS-794-TEG will generally have better solubility in water than PSS-794.

UV spectra of PSS-794 and PSS-794-TEG show a sharp peak at 798 nm in methanol and similar fluorescence spectra. Table 1 provides details of the absorption and emission properties in water.

TABLE 1

The absorption and emission properties of dyes in water

| | Dyes | |
|---|---|---|
| | PSS-794-Zn | PSS-794-TEG-Zn |
| $\lambda abs/nm$ | 794 | 794 |
| $\lambda em/nm$ | 810 | 812 |
| $\epsilon/$ | $1.1 \times 10^5$ | $2.5 \times 10^5$ |

In an embodiment, there is provided a method for selectively detecting (staining) apoptotic cells in a sample, such as a mixed population of apoptotic and non-apoptotic cells, or in a tissue, including a living tissue. In some embodiments, the method may be used in the selective imaging of cancerous tissues. In some embodiments the method may be described as suitable for detecting, selecting and/or identifying cells in any stage of early to late apoptosis, apart from necrotic cells or healthy cells.

In an embodiment, there is provided a method of detecting the presence of bacterial cells. In a related embodiment, there is provided a method of detecting the presence of bacterial cells in a sample, such as a mixed population of bacterial cells and nonbacterial cells. Such an embodiment may be further utilized to locate an infection by imaging the accumulation of bacterial cells at an infection site.

In an embodiment, there is provided a high throughput screening method for selecting anti-cancer compounds that induce apoptosis. These methods, and the candidate substances selected using this method, may then be used, for example, to identify anti-cancer agents for destroying and/or inhibiting cancerous cells and cancerous cell proliferation and/or spreading.

In some embodiments, a method comprises selecting potential apoptosis-inducing substances from a pool of candidate substances by selecting those substances in the pool of candidate substances that increase the level of phosphatidylserine on the surface of cells, as measured by the amount of PSS-480, PSS-794 or other probe(s) on a cell after being exposed to the candidate substance. In some embodiments, the cell is a human cell. In particular screening and/or selection methods, the cells are Jurkat cells, HeLa cells or Breast Cancer cells.

In an embodiment, there is provided a method for selecting a substance capable of inhibiting apoptosis. For example, a pool of potential substances for inhibiting apoptosis may be screened for apoptosis inhibiting activity by examining the level of progression and/or inhibition of apoptosis that occurs in a culture of cells that have been previously, concurrently, or subsequently exposed to an apoptotic substance or to apoptotic inducing conditions. A comparison may then be made of the relative rate and/or amount of apoptosis that occurs in a culture of cells receiving the candidate substance and the culture of cells that did not receive the candidate substance. A potential anti-apoptotic substance may then be selected from the pool of substances that results in a reduced rate and/or amount of apoptosis in the treated cell culture, relative to the untreated (control) cell culture. Substances that reduce apoptosis rate and/or progression by at least 20% or more may then, for example, be selected.

In some embodiments, the reporter element is a fluorescein and the molecule is called PSS-480. In other embodiments, the detectable reporter element is biotin, which may be detected using a labeled streptavidin protein. In other embodiments, the reporter element is a highly luminescent quantum dot (QD). Among other advantages, these embodiments provide the additional advantage of providing multivalent binding to a cell membrane surface.

In an embodiment, there is provided a method for screening and/or selecting anti-apoptotic substances specifically using PSS-480, PSS-794, or other probe(s) as the phosphatidylserine sensing molecule. In some embodiments, this method may include an operation in which a candidate substance may be selected that is observed in a cell culture to induce a lower amount of detectable fluorescence (for example, when using PSS-480) after exposure to the candidate substance, compared to detectable fluorescence observed in a cell culture that is not exposed to the candidate substance.

Another embodiment provides a tool that may be incorporated as part of a clinical regimen in assessing the efficacy of an anti-cancer agent in a patient. For example, periodic screening of a patient's tissue may be performed at defined intervals before, during and after a defined treatment regimen, and the relative effectiveness of an agent being administered during the treatment regimen may be assessed by the presence, absence, or relative decrease or increase of the relative percentage or number of apoptotic cells/cancer cells in the patient sample.

In an embodiment, there is provided an improved apoptotic cell and/or cancer cell surface indicator agent having improved properties relative to annexin. By way of example, such improved properties include the ability to sense and/or detect the presence of phosphatidylserine on the surface of apoptotic cells under relatively calcium-free conditions, that is in the presence of less than about 500 μM, or 100 μM, or 50 μM, etc. calcium conditions. An additional improved property of the herein described phosphatidylserine sensitive molecules is their relatively lower dissociation constant for phosphatidylserine that may be expressed as a Kd of $10^{-6}$ M or less, $10^{-5}$ M, $10^{-4}$ M, $10^{-3}$ M, or even $10^{-2}$ M or less.

In other embodiments, there is provided a method for preparing a phosphatidylserine sensing molecule, such as PSS-480, PSS-794, PSS-794-TEG, PSS-Biotin, and PSS-QD.

EXAMPLES

Example 1

Synthesis of PSS-480 diacetate: The fluorescein-labeled compound PSS-480 was prepared by coupling the amine as shown below with 5-carboxyfluorescein diacetate. Subsequent deprotection using ammonium hydroxide followed by treatment with $Zn(NO_3)_2$ in aqueous methanol gave PSS-480 as its bis(ammonium) salt.

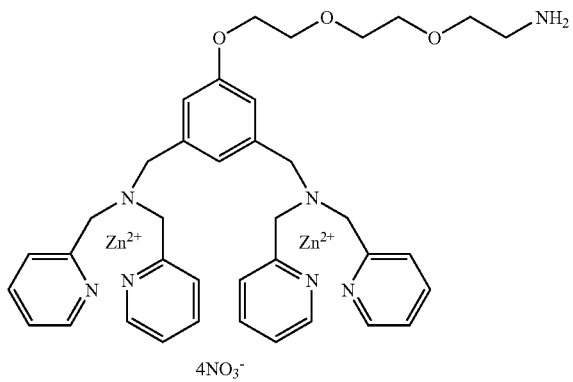 [SMILES: NCCOCCOCCOc1cc(CN(Cc2ccccn2)Cc2ccccn2)cc(CN(Cc2ccccn2)Cc2ccccn2)c1 ; [Zn+2] ; [Zn+2]]

5-Carboxyfluorescein diacetate (0.097 g, 0.21 mmol) was added to a solution of N-hydroxysuccinimide (0.37 g, 0.32 mmol) and 1-ethyl-3-(3-dimethylaminopropyl)-carbodiimide hydrochloride salt (EDC; 0.61 g, 0.32 mmol) in dry $CH_2Cl_2$ under Ar. The reaction mixture was stirred overnight, then washed with water and brine and dried over $Na_2SO_4$. The solvent was removed under vacuum, and the residue was separated by chromatography on a silica column with $CHCl_3$/MeOH (92:8) as the eluent. Yield: 31%; $^1H$ NMR (300 MHz, $CDCl_3$); δ=2.31 (s, 6H), 3.62 (br, 4H), 3.72 (m, 6H), 3.78 (M, 10H), 3.91 (m, 2H), 4.18 (m, 2H), 6.71-6.80 (m, 4H), 6.88 (s, 2H), 7.04 (s, 1H), 7.09-7.14 (m, 5H) 7.19 (m, 2H), 7.30 (s, 1H), 7.54-7.64 (m, 8H), 8.20 (m, 1H), 8.43 (br, 1H), 8.48-8.50 (m, 4H), $^{13}C$ NMR (75 MHz, $CDCl_3$): δ=21.3, 40.3, 58.7, 60.1, 67.6, 69.9, 70.0, 70.6, 71.0, 110.7, 113.9, 116.0, 118.1, 122.1, 122.4, 123.0, 123.3, 123.7, 124.7, 126.7, 129.0, 135.0, 136.7, 137.2, 140.7, 148.9, 149.1, 151.7, 152.4, 155.2, 159.0, 159.7, 165.7, 168.4, 169.0; FAB MS m/z 090 $[M+H]^+$.

PSS-480 diacetate (0.03 g, 0.028 mmol) was dissolved in MeOH (0.5 mL) and treated with $NH_4OH$ (0.5 mL). The reaction mixture was stirred at 40° C. overnight. The solvents were then removed under vacuum, the residue washed with water (4×) and dried under high vacuum to yield 0.018 g (60%) of diammonium salt. The removal of acetoxy groups was confirmed by 1H NMR. The $Zn^{2+}$ complex was prepared by mixing a solution of diammonium salt (0.018 g, 0.17 mmol) in methanol and an aqueous solution of zinc nitrate (0.01 g, 0.35 mmol). After 30 minutes of stirring, the solvents were removed under vacuum, and the residue lyophilized to yield the zinc complex in quantitative yield.

Example 2

The above example demonstrates at least one method that may be employed in the preparation of PSS-480, as well as other species of the PSS-fluorescein derivative molecules described herein. However, other techniques and/or substitutions for the conditions and reagents described herein will be immediately apparent to those of skill in the art in the preparation of these and similar preparations in accordance with the disclosure provided herein.

Example 3

Preparation of PSS-Biotin: The present example demonstrates at least one method that may be employed in the preparation of the PSS-biotin preparations of the invention, as well as other species of the PSS-reporter complexed molecules described herein. However, other techniques and/or substitutions for the conditions and reagents described herein will be immediately apparent to those of skill in the art in the preparation of these and similar preparations in accordance with the disclosure provided herein.

1-Hydroxy 1H-benzotriazole (0.14 g, 1 mmol) and EDC 14 g, (0.19 g, 1 mmol) were added to a solution of biotin (0.24 g, 1 mmol) in dry DMF under an Ar atmosphere. Amine 1 (0.65 g, 1 mmol) in dry $CH_2Cl_2$ was added, and the reaction mixture was stirred for 2 d. The solvent was then removed under vacuum, and the reaction mixture was taken up in $CHCl_3$. The $CHCl_3$ layer was washed with sat. $NaHCO_3$, water, and brine and dried over anhydrous $MgSO_4$. The solvent was removed under vacuum, and the residue was separated by chromatography on a neutral alumina column with $CHCl_3$/MeOH (98:2) as the eluent. The overall yield of the uncomplexed compound was 60%. Selected data: $^1H$ NMR (300 MHz, $[D_6]$DMSO): δ=1.2-1.64 (m, 6H), 2.03 (m, 2H), 2.55 (d, J=12.3 Hz, 1H), 2.76-2.82 (q, J=5.1 Hz, 1H), 3.05-3.09 (m, 1H), 3.39 (m, 2H), 3.51-3.53 (m, 2H), 3.57 (m, 6H), 3.70-3.74 (m, 10H), 4.04-4.14 (m, 5H), 4.26-4.30 (m, 1H), 6.36 (s, 1H), 6.42 (s, 1H), 6.83 (s, 2H), 7.08 (s, 1H), 7.22-7.26 (m, 4H), 7.57 (d, J+7.8 HZ, 4H), 7.70-7.76 (m, 4H), 7.83 (t, J=5.4 Hz, 1H), 8.47-8.49 (m, 4H), $^{13}C$ NMR (75 MHz, $[D_6]$DMSO): δ=25.3, 28.0, 28.2, 35.1, 38.4, 48.6, 55.4, 57.4, 59.2, 61.0, 66.9, 68.9, 69.2, 69.6, 69.8, 113.2, 121.0, 122.2, 122.4, 136.6, 140.2, 148.8, 158.4, 159.2, 162.7, 172.1; FAB MS m/z 874 $[M+H]^+$.

The uncomplexed compound (0.87 g, 1 mmol) was linked with biotin by coupling with the amine from Example 1 and biotin, followed by complexation with zinc nitrate, $Zn(NO_3)_2$) (0.61 g, 2.05 MMOL) in aqueous methanol. This solution was stirred for 0.5 h. The solvents were removed under vacuum, and the resulting biotin-linked compound, PSS-biotin, was used without further purification.

Example 4

Preparation of Carboxy-Peg Encapsulated Quantum Dots: The present example demonstrates at least one method that may be employed in the preparation of the carboxy-PEG encapsulated quantum dot preparations of an embodiment of the invention. However, other techniques and/or substitutions for the conditions and reagents described herein will be immediately apparent to those of skill in the art in the preparation of these and similar preparations in accordance with the disclosure provided herein.

Octadecyl-amine-stabilized CdSe/CdS core/shell nanocrystals (QDs; typical UV absorption $\lambda_{max}$~550 nm) were prepared by following existing literature methods and redissolved in chloroform to provide a stock solution of 150 $mg/mL^{-1}$.

The organic soluble QDs were then encapsulated in carboxy-PEG-phospholipid micelles to render them water soluble. More specifically, an aliquot (300 µL) of the QD stock solution (150 mg $mL^{-1}$) was combined with a solution (~1 mL) of chloroform containing 1,2-distearoyl-sn-glycero-3-phos-phosphoethanolamine-N-[carboxy poly(ethylene glycol)2000] ammonium salt (0.0165 g, $5.8 \times 10^6$ mol). After complete evaporation of the chloroform (by careful heating with stirring), the residue was further warmed to −80° C. in a water bath for 1-2 min, after which time, double deionized water (1 mL) was added with vigorous stirring. The sample was stirred for 1-2 min at ~80° C. and then sonicated at RT for 10 min to give an optically transparent solution. The sample was then centrifuged at 5000 rpm for 10 min to pellet out any unencapsulated or aggregated particles. The supernatant was transferred to a new vial and centrifuged at 500,000 g for 2 h to separate/pellet out the phospholipid-encapsulated QDs from the empty micelles remaining in the supernatant. The supernatant was carefully removed, and the QD-micelle pellet was resuspended in phosphate buffer (500 µL, pH 7.4).

The supernatant containing the excess phospholipid micelles was frozen with liquid nitrogen and lyophilized to determine the approximate amount of recovered phospholipids. The amount of phospholipid incorporation in the QD micelles could then easily be determined. In general, ~33% of the phospholipids were found to be utilized in the encapsulation of the QDs, giving ~$1.9 \times 10^{-6}$ mol of total phospholipid per 500 µL of QD solution.

Figure 7A:
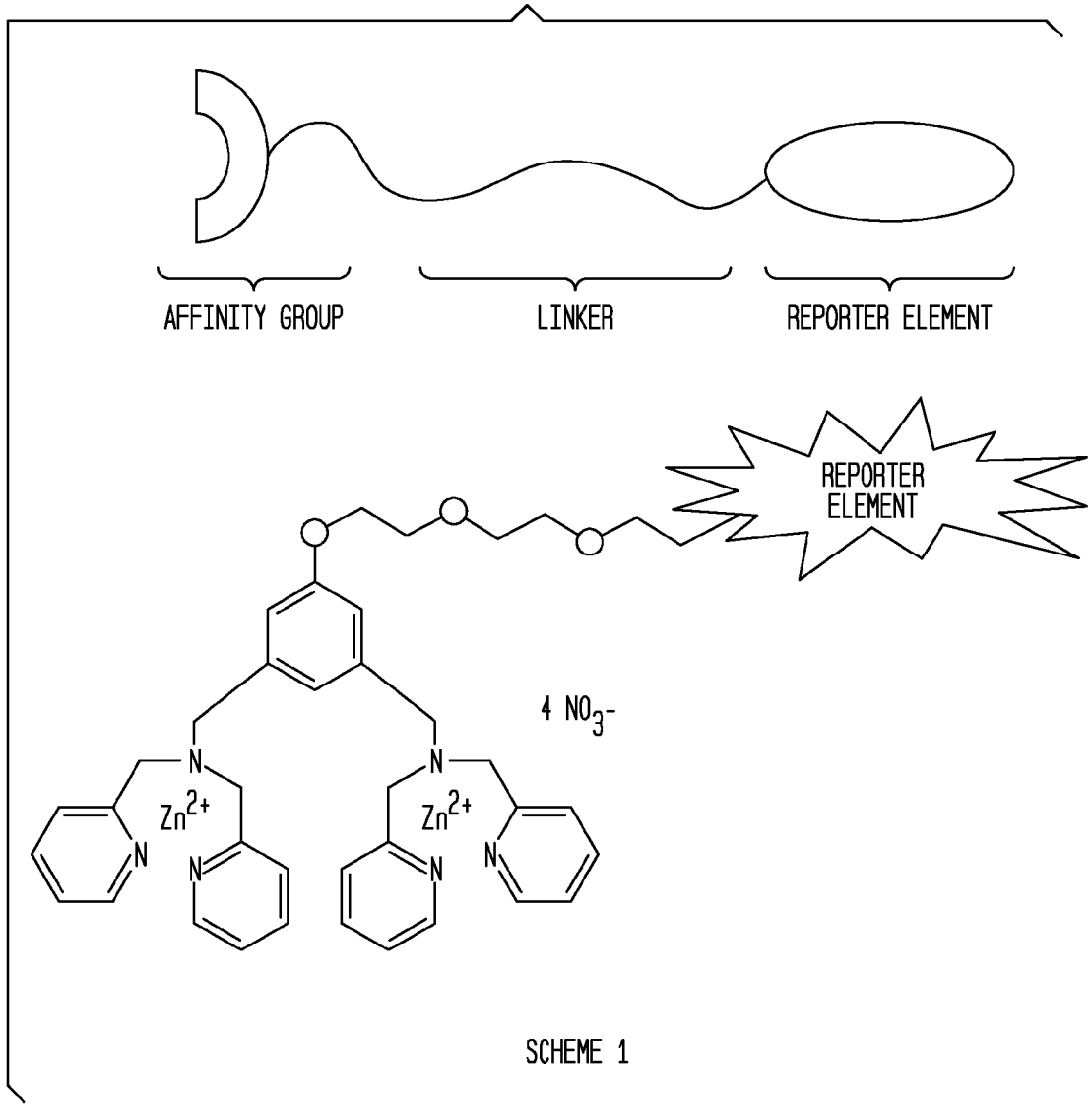
FIGS. 7A-7C present a Scheme 1 (7A), Scheme 2 (7B) and Scheme 3 (7C) of the coordination complexes of embodiments of the invention.
Figure 7B:
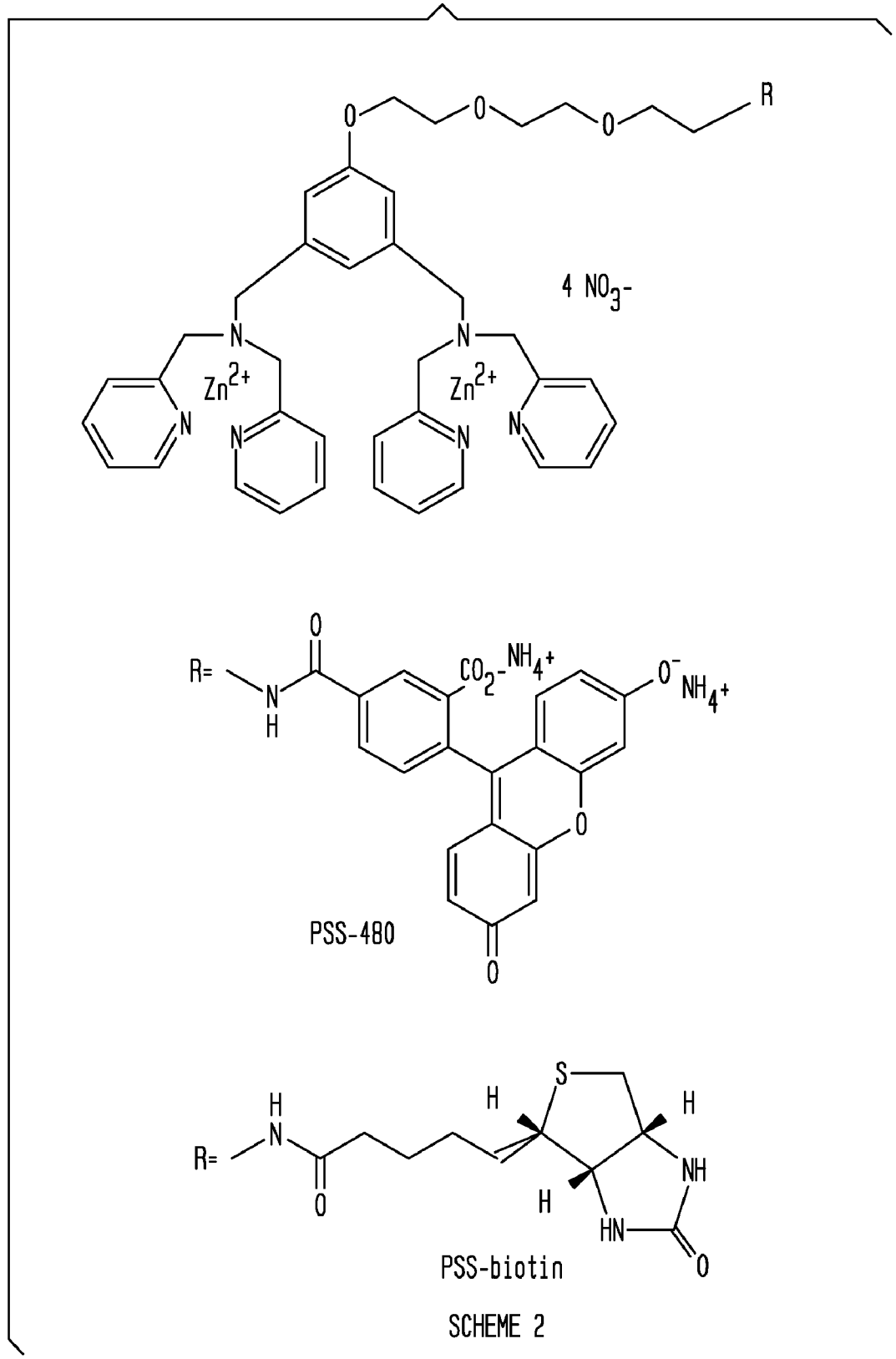
Figure 7C:
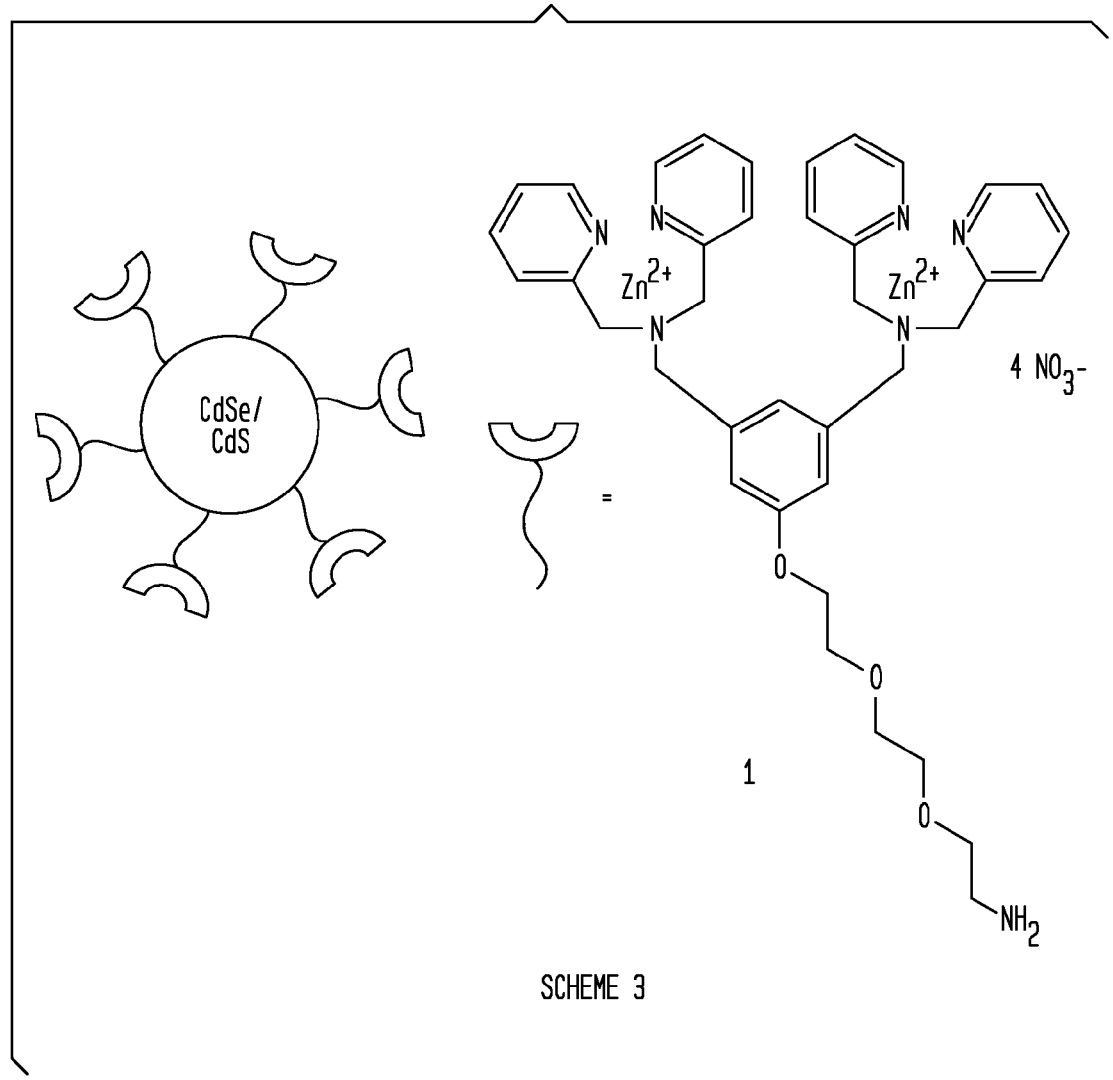
Figure 8A:
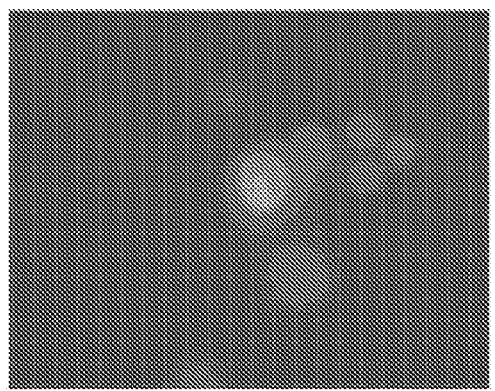
FIGS. 8A-8D present fluorescence micrographs (60× magnification) of Chinese Hamster Ovary (CHO) cells treated with camptothecin (10 μM) for 3.5 h to induce apoptosis, then stained with PSS-480 (15 μM) and the nuclear stain 7AAD (500 ng/mL). Fluorescence of cells stained with 7AAD is shown in FIG. 8A.
Figure 8B:
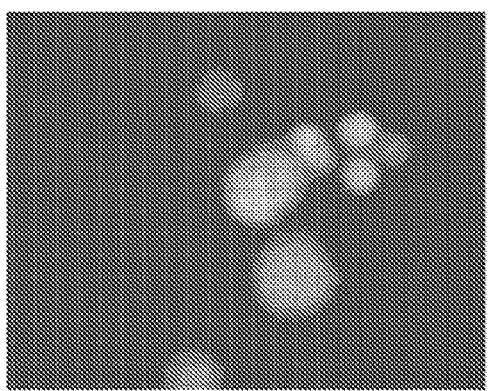
Figure 8C:
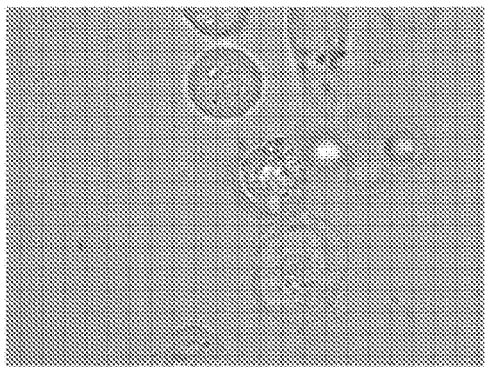
Figure 8D:
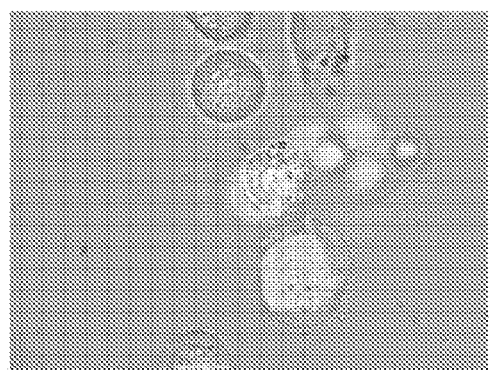
Figure 9A:
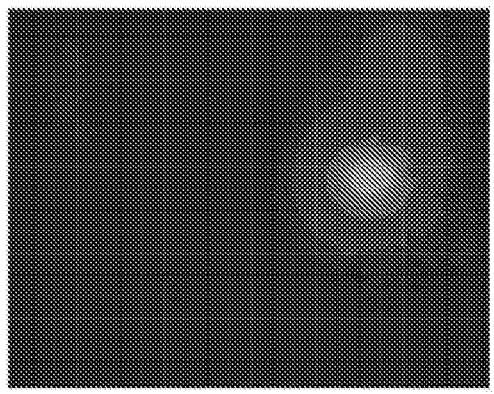
FIGS. 9A-9D present fluorescence micrographs (60× magnification) of HeLa cells treated with camptothecin (10 μM) for 3.5 h to induce apoptosis, then stained with PSS-480 (15 μM) and the nuclear stain 7AAD (500 ng/mL). Fluorescence of cells stained with 7 AAD is shown in FIG. 9A.
Figure 9B:
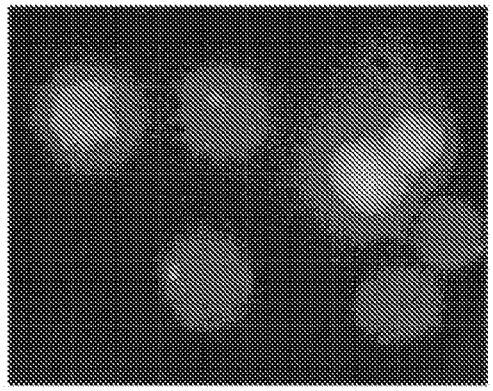
Figure 9C:
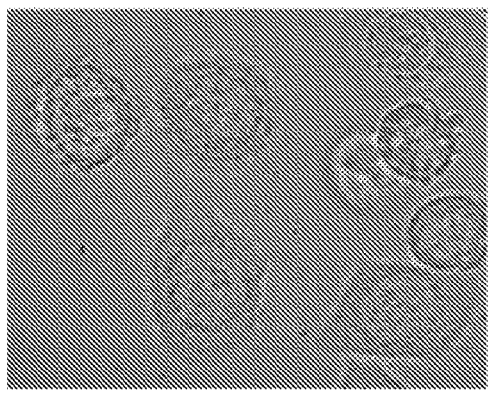
Figure 9D:
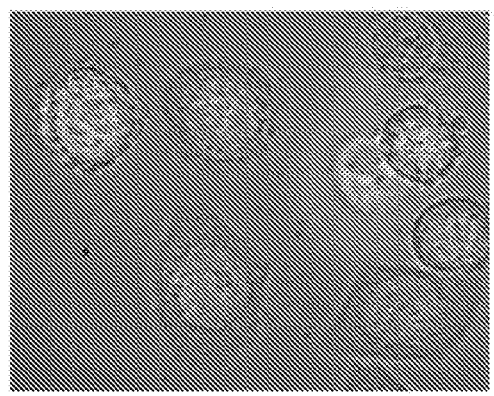
Figure 10:
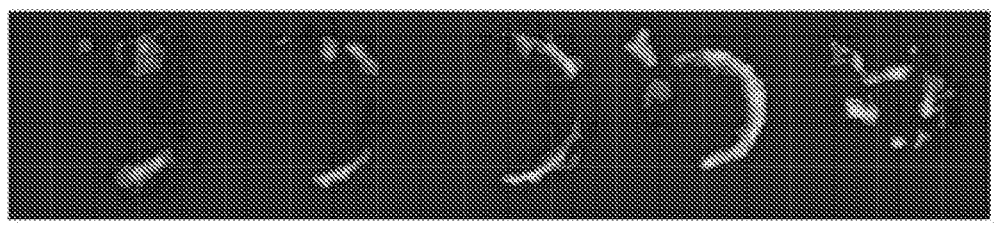
FIG. 10 presents cell surface labeling of a single Jurkat cell from a population treated with camptothecin (10 μM) for 3.5 h to induce apoptosis. Images are 0.5 μM slices (60× magnification) taken through the cell separated by 2.5 μm. Cells were treated with 10 μM PSS-Green-QD. Exclusion of PSS-Green-QD from the interior of the cell indicates that only surface staining takes place.
Figure 11A:
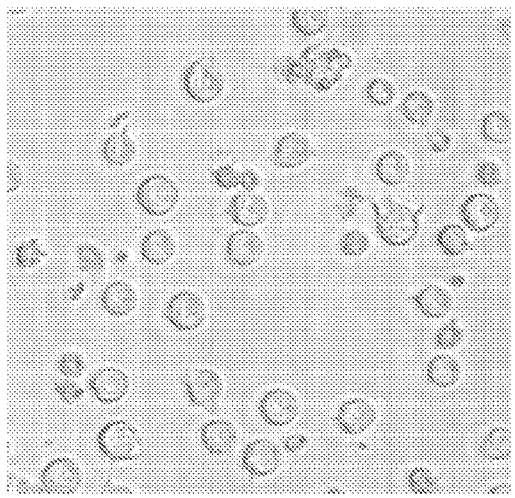
FIGS. 11A-11D present fluorescence images and phase contrast images of Jurkat cells.
Figure 11B:
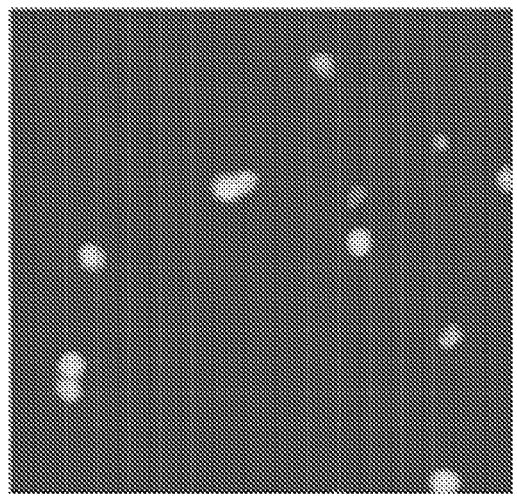
Figure 11C:
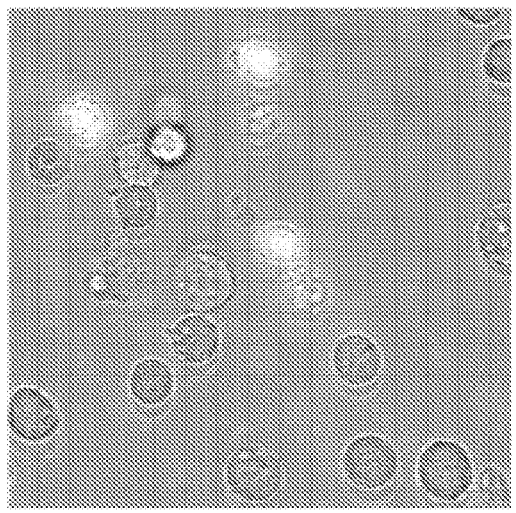
Figure 11D:
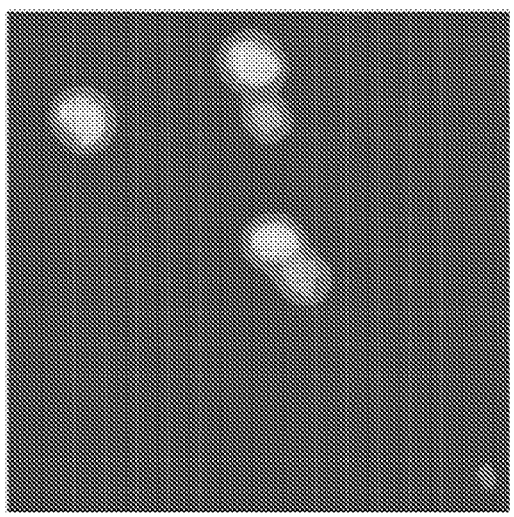

Transmission electron microscopy showed that the quantum dots were of uniform diameter (~4-5 nm) and not aggregated (FIG. 1). These organic soluble nanoparticles were subsequently encapsulated in carboxy-PEG-phospholipid micelles, rendering them water soluble. The exposed carboxyl residues were coupled with the bis-$Zn^{2+}$ complex of amine (see Example 1) to give $Zn^{2+}$-DPA-conjugated micelle encapsulated quantum dots (PSS-Green QD) (FIG. 7C, Scheme 3).

Example 5

Preparation of Pss-Green Qd: the present example demonstrates at least one method that may be employed in the preparation of the PSS-Green QD preparations of the invention. However, other techniques and/or substitutions for the conditions and reagents described herein will be immediately apparent to those of skill in the art in the preparation of these and similar preparations in accordance with the disclosure provided herein.

Ethyl-3-(3-dimethylamineopropyl)carbodiimide hydrochloride salt (EDC, 7.6 mg, $4.0 \times 10^{-5}$ mol), N-hydroxysulfosuccinimide (sulfo-NHS, 5.7 mg, $3.0 \times 10^{-5}$ mol), and the preformed $Zn(NO_3)_2$ complex of amine 1 ($1.22 \times 10^{-5}$ mol) were dissolved in the carboxy-PEG micelle-encapsulated QD solution [500 μL in phosphate buffer (pH 7.4)]. The resulting solution was mixed with mild agitation for 2 h and then purified by dialysis (Spectra/POR®, 50000 MWCO) against double deionized water for 24 h to provide the $(Zn^{2+})_2$-DPA-PEG micelle-encapsulated quantum dots. The aqueous QD solution was stored at $-24°$ C. in the dark until needed. These solutions exhibited no flocculation and retained their PS binding capability for at least one month.

Example 6

Transmission Electron Microscopy: The present example demonstrates the utility of an embodiment of the present invention as a clinical tool in the assessment of apoptotic cells in a mixed population of cells using transmission electron microscopy (TEM).

TEM samples were prepared by allowing a small drop of a chloroform nanoparticle solution on a copper-coated TEM grid to evaporate by air. The TEM images were obtained from a Philips CM30 microscope at 300 kV.

As demonstrated in FIG. 1, the PSS-480 agents are useful in standard TEM techniques.

Example 7

Cell staining and Fluorescence Microscopy in Jurkat Cells: The present example demonstrates the utility of an embodiment of the present invention as a selective clinical tool for the identification of apoptotic cells in a population of apoptotic and non-apoptotic cells. An embodiment of the present invention also demonstrates the utility as a powerful selective imaging agent for staining cancer cells in a tissue, as it demonstrates the use of the agent to selectively stain apoptotic cells (cancer cells) in a mixed population of cells comprising a human cancer cell line, Jurkat cells.

Annexin V and 7AAD were obtained from BD Biosciences (San Jose, Calif.). Quantum dot-streptavidin conjugates were from Quantum Dot Corporation (Hayward, Calif.). The Marina Blue streptavidin conjugate was from Molecular Probes (Eugene, Oreg.). Jurkat cells were grown to a density of approximately $1.0 \times 10^6$ $mL^{-1}$ in RPMI 1640, 10% FCS at 37° C., 5% $CO_2$. A 10 mL volume of cells was treated with camptothecin (10 μM final concentration) in growth medium for 3.5 h at 37° C., 5% $CO_2$. Cells were spun down and resuspended in 1× annexin binding buffer (10 mM HEPES sodium salt, 2.5 mM $CaCl_2$, 140 mM NaCl, pH 7.4) for studies in which annexin V was used, or in a buffer of N-tris (hydroxymethyl)methyl-2-aminoethanesulfonic acid (TES; 5 mM), NaCl (145 mM), pH 7.4 for studies in which annexin V was not used. Aliquots (0.5 mL) of the treated cells, along with controls; were then treated with the indicated staining reagents at the indicated concentrations. Annexin V-FITC was used according to the manufacturer's protocol (BD Biosciences). All reagents were added simultaneously. The cell suspensions were mixed thoroughly by repeated inversion and then incubated 15 min at 37° C., except where temperature effects were being evaluated. Cells were then centrifuged, resuspended, and washed twice in TES (5 mM), NaCl (145 mM)), pH 7.4 buffer. At this point, 250 μL of the suspension was transferred to a 16-well chamber slide for microscopy.

Fluorescence microscopy was performed immediately following cell staining on an Axiovert S100 TV microscope (Carl Zeiss) equipped with filter sets DAP/Hoechst/AMCA, FITC/RSGFP/Bodipy/Fluo3/DiO, Cy3 (Chroma, Rockingham, Vt.). Pictures were taken on a black and white digital camera (Photometrics, Tucson, Ariz.) and colored afterwards by using Photoshop 6.0 software (Adobe).

Fluorescence microscopy was used to demonstrate that PSS-480, PSS-Biotin, and PSS-Green QD selectively stain apoptotic cells.

Jurkat cells were treated first with camptothecin (an anticancer drug), to induce apoptosis, and then simultaneously with PSS-480 and nuclear stain 7AAD (7-amino-acitomycin D) (FIGS. 2A-2D). Necrotic cells, as well as those cells in the advanced stages of apoptosis, have permeabilized membranes, and allow 7AAD to stain the nucleic acid. Healthy cells, and those cells in the early to intermediate stages of apoptosis, retain their membrane integrity and exclude 7AAD. This allows cells in early apoptosis to be identified by selective staining with PSS-480 and exclusion of 7AAD. A brightfield image of a field of cells stained with PSS-480 (FIG. 2D) clearly illustrates that the PS affinity group binds only to those cells with externalized PS. Similarly, PSS-480 was used to identify HeLa and CHO cells exposing PS on the membrane surface (See FIGS. 8A-8D, FIGS. 9A-9D, FIG. 10, and FIGS. 11A-11D).

Evidence that the PS-affinity group is binding to the same membrane sites as Annexin V is provided in FIGS. 3A-3D, which illustrates the co-staining of apoptotic Jurkat cells with 7 AAD, annexin V-FITC, and the biotinylated probe PSS-Biotin, visualized using a blue-emitting streptavidin conjugate. The circled cells are apoptotic, evidenced by their staining only with annexin V and PSS-Biotin/streptavidin with simultaneous exclusion of 7AAD.

Figure 4:
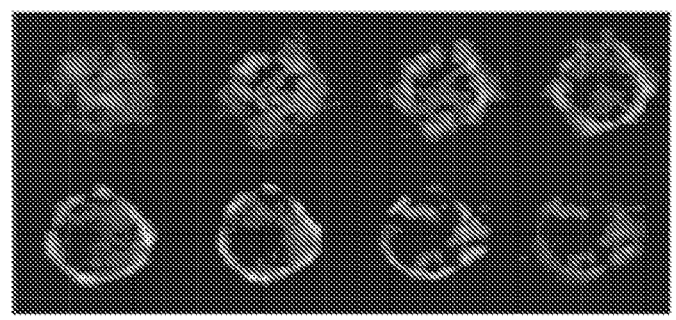
FIG. 4 presents cell surface labeling of Jurkat cells treated with 10 μM camptothecin for 3.5 h to induce apoptosis. Images are 0.5 μM slices (60× magnification) taken through the cell separated by 2.5 μM. Cells were treated with annexin V-FITC and PSS-biotin (100 uM) with a red-emitting (605 nM) streptavidin-quantum dot conjugate (10 nM). The lighter colored areas are a result of annexin V-PSS biotin/streptavidin-quantum dot colocalization.
Figure 5A:
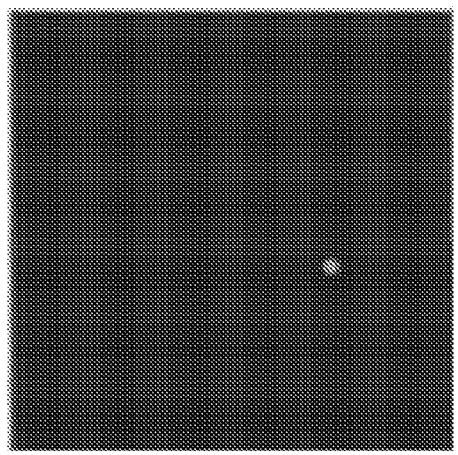
FIGS. 5A-5D present fluorescence micrographs (40× magnification) of Jurkat cells treated with camptothecin (10 μM) for 3.5 h to induce apoptosis, then stained with PSS-Green QD (2.75 μM) and 7AAD (500 ng $mL^{-1}$). 5A) Fluorescence of cells stained with 7 AAD; B) fluorescence of cells stained with PSS-Green QD; and 5C) an overlay of (5A) and (5B). Those cells stained only with PSS-Green QD are apoptotic as illustrated by exclusion of 7AAD. 5D) A phase-contrast image of all cells in the field. No staining of healthy cells was observed in the absence of treatment with camptothecin.
Figure 5B:
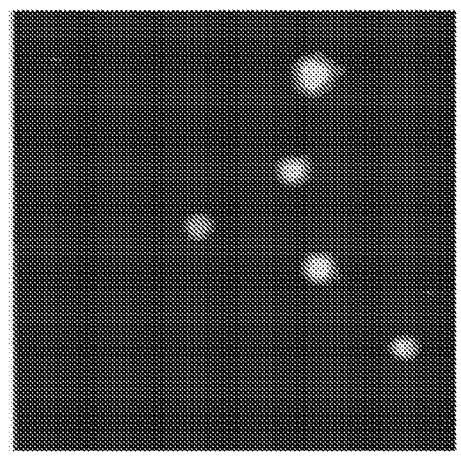
Figure 5C:
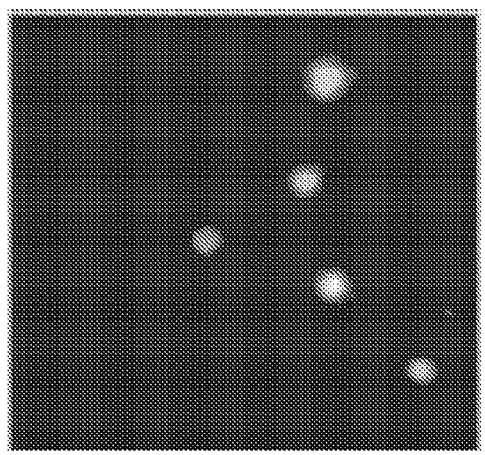
Figure 5D:
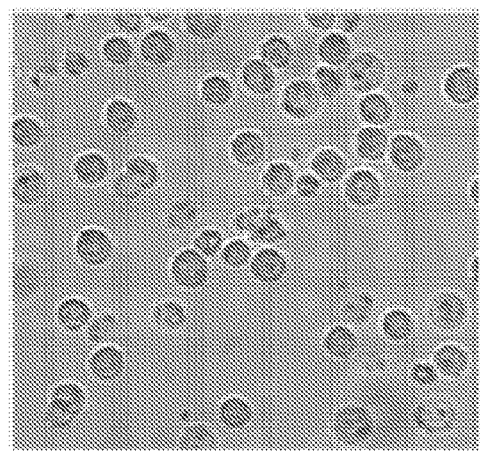

Additional co-staining evidenced is supplied in FIG. 4, which shows fluorescent cross sections of a single Jurkat cell treated with annexin V-FITC and PSS-biotin visualized with a red-emitting streptavidin-quantum dot conjugate. The staining is clearly restricted to the exterior cell membrane, and the yellow-orange color signifies colocalization.

FIG. 5 demonstrates that selective staining of cells with externalized PS was also observed with PSS-Green QD.

Cross sectional micrographs showed that the staining was restricted to the exterior membrane (see FIGS. 8A-8D, FIGS. 9A-9D, FIG. 10, and FIGS. 11A-11D). Control studies indicated that quantum dots coated with ammonium groups instead of the PS-affinity groups do not stain apoptotic cells.

Figure 6:
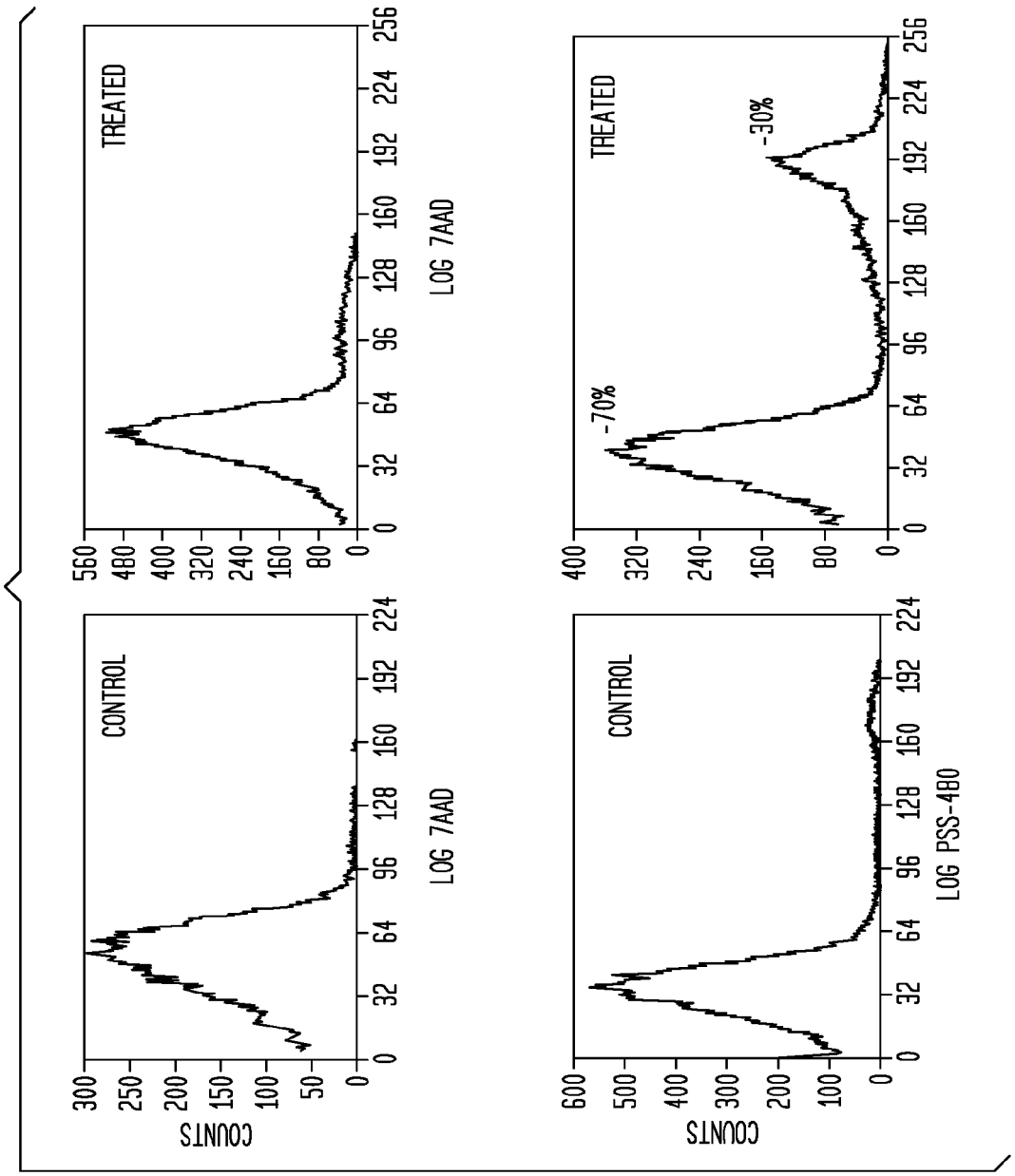
FIG. 6 presents flow-cytometry graphs illustrating staining of Jurkat cells by PSS-480 and 7AAD. Both control and treated cells exhibit similar levels of staining by 7AAD; this indicates that there is the same level of necrotic cells in the population (less than 5% in each case). Cells treated with camptothecin exhibit significantly more staining by PSS-480 than do control cells. Approximately 30% of treated cells were identified as apoptotic by using PSS-480, while less than 5% of the untreated cells were stained with PSS-480.

The histograms in FIG. 6 indicate that approximately 30% of the cells were stained with PSS-480. With untreated cells, less than 5% of the total population was stained with PSS-480.

Example 8

Flow Cytometry in Jurkat Cell Line: The present example demonstrates the utility of an embodiment of the present invention for use with Jurkat cells, a human leukemia cell line, and hence utility in the treatment and/or clinical management of leukemia and leukemia-like cancers.

Jurkat cells were cultured according to the same procedures described for fluorescence microscopy. A 10.0 mL volume of cells was treated with camptothecin (10 µM final concentration) in growth medium for 16.5 h at 37° C., 5% $CO_2$.

Cells were spun down and resuspended in 1× annexin binding buffer (10 mM HEPES sodium salt, 25 mM $CaCl_2$, 140 mM NaCl, pH 7.4). For studies in which annexin V was used, or in a buffer of TES (5 mM), NaCl (145 mM), pH 7.4 for experiments in which annexin V was not used. Cell aliquots (1.0 mL) were stained with 7AAD (500 ng $mL^{-1}$) and either PSS-480 (5 µM) or annexin V-FITC (5 µL $mL^{-1}$; BD Biosciences commercial solution). All reagents were added simultaneously. The cell suspensions were mixed thoroughly by repeated inversion and then incubated 15 min at 37° C., except where temperature effects were being evaluated. Cells were then centrifuged, resuspended, and washed twice in TES (5 mM), NaCl (145 mM)), pH 7.4 buffer. Flow cytometry was performed immediately after staining on an Epics XL flow cytometer (Coulter, Miami, Fla.) with an argon laser. FITC was analyzed by using a 520 nm bandpass filter, and 7AAD was analyzed by using a 580 nm bandpass filter. Software color compensation was used and data analysis was performed by using Multiplus AV Software (Phoenix Flow Systems, San Diego, Calif.).

Example 9

$Zn^{2+}$-DPA Coordination Complexes as Clinical Tools in Jurkat Cells: The present example demonstrates the utility of an embodiment of the present invention as a clinical tool for the detection, treatment and monitoring of apoptosis and cancer in human cells and tissues, employing a human leukemia cell line, a Jurkat cell line. The present example also demonstrates the utility of an embodiment of the invention as a clinical diagnostic and screening tool in the absence of calcium and/or in a calcium-free assay.

During apoptosis, the electrostatic charge on a cell membrane surface becomes increasingly negative as the PS normally confined to the inner monolayer becomes distributed between the inner and outer leaflets. The ability of $Zn^{2+}$-DPA coordination complexes to selectively bind to negatively charged membranes is an effective strategy for recognizing cells in the early to middle stages of apoptosis. The $Zn^{2+}$-DPA coordination complexes presented in embodiments of the present invention circumvent limiting features of annexin V. For example, binding of the PS-affinity group to apoptotic cell membranes is $Ca^{2+}$-independent, the binding is virtually instantaneous, and the fluorescein in PSS-480 is compatible with the argon lasers found in commonly used flow cytometers. Furthermore, the presence of up to 10% serum in the binding medium has no adverse effect on staining, and the apoptotic cells are successfully stained by PSS-480, PSS-Biotin, and PSS-Green QD at temperatures from 4° to 37° C. with incubation periods as short as 30 seconds (see FIGS. 8A-8D, FIGS. 9A-9D, FIG. 10, and FIGS. 11A-11D). Similar results could not be obtained when fixed cells were used, and a nearly homogeneous staining of the cytosol of Jurkat cells was observed when cells were stained with PSS-480 after ethanol fixation.

The versatile PSS-Biotin allows PS detection by a wide range of commercially available streptavidin-fluorophore conjugates. For example, the quantum dot-streptavidin conjugates are well suited for fluorescence microscopy because of the high quantum yield common to quantum dots, as well as the ability of the quantum dots to resist photo bleaching. A simplification of the quantum dot system was achieved by directly conjugating the PS-affinity group to micelle-encapsulated CdSe/CdS quantum dots, affording a PS-selective stain (PSS-Green QD) that can withstand prolonged exposures without diminished fluorescence intensity. In addition, the quantum dot system may exhibit enhanced binding due to multivalency effects.

A greater number of washings must be performed after staining cells with PSS-Green QD. The extreme brightness of the quantum dots means that a very high fraction of the unbound material must be eliminated in order to achieve a suitably dark background.

The PS-affinity group used in all three probes binds only to the apoptotic cell surface. The fact that only surface binding is observed indicates that no membrane permeabilization has taken place, signaling that the cells have not yet progressed to the later stages of apoptosis. The exclusion of PSS-Green QD from the cell interior is noteworthy considering that other systems have been reported to cross the membranes of other cell lines when incubated for longer periods. Another salient point is the difference in photophysics between the coordination complexes described here and PSS-380. Association of PSS-380 to a PS-rich membrane leads to fluorescence enhancement, due to enhanced binding of $Zn^{2+}$ to the DPA units in PSS-380 which decreases PET quenching. In contrast, the PET quenching pathway is not significant in PSS-480 and control studies with vesicles show that association of PSS-480 with PS-rich membranes does not alter its fluorescence intensity. Similarly, the fluorescent probes presented here act in the same way as annexin V-FITC, that is, they are PS-selective strains that require a washing step to remove the unbound material.

Embodiments of the present invention show how $Zn^{2+}$-DPA coordination complexes may be developed into effective fluorescent probes for apoptosis. The two $Zn^{2+}$-DPA subunits selectively bind to membranes enriched in anionic PS. The versatility of the system is enhanced by attaching a biotin reporter element (PSS-Biotin), making detection of apoptotic cells possible with a range of streptavidin conjugates. The $Zn^{2+}$ coordination complexes allow users to identify apoptotic cells under $Ca^{2+}$ free conditions and with fast binding kinetics, which broadens the scope of PS-detection methods for apoptosis. The low molecular weight, non-protein probes presented may be adaptable to other imaging techniques, such as radiography and magnetic resonance spectroscopy. For purposes of describing embodiments of the present invention, the term "low molecular weight" refers to constructs having less than 5000 MW (g/mole), such as less than 1000 MW, or even, in embodiments, less than 500 MW.

Example 10

Measurements of PS Dissociation Constants: The ideal candidate for apoptosis detection via externalized PS should have a strong affinity for anionic PS embedded in an animal cell membrane that is primarily composed of zwitterionic phospholipids. In an embodiment, the sensor binding, however, must not disrupt the membrane structure. PSS-480 was found to be incapable of inducing bilayer permeabilization. Specifically, addition of PSS-480 at concentrations up to 10 µM to vesicles composed of either 100% POPC or 1:1 POPC: POPS failed to induce carboxyfluorescein leakage.

An analogue of PSS-480 was used to measure PS dissociation constants. The analogue has an NBD fluorophore that is known to exhibit an enhancement in fluorescence intensity upon transfer from a polar environment to an apolar environment. Thus, the fluorescence emission was expected to increase upon binding to the surface of a bilayer membrane. Indeed, titration of the NBD analogue with anionic vesicles produced moderate to large fluorescence enhancements. The resulting isotherms were fitted to a 1:1 binding model, which allowed calculation of apparent phospholipid dissociation constants. The order of binding affinities to vesicles was 1:1 POPC:POPS<1:1 POPC:POPG~1:1 POPC:POPA<<100% POPC.

When the membrane contains 100% PC which mimics a healthy cell, the Kd is about $10^{-2}$ M. But when the membrane contains 5% PS and 95% PC which is the approximate fraction of PS that is externalized during the early-to-intermediate stages of cell apoptosis, the Kd is $10^{-4}$ M. These results demonstrate that selective fluorescent staining of the membranes of apoptotic cells may be achieved with PSS compounds that have Kd<$10^{-4}$ M, as long as the Kd for healthy cell membranes is more than ten times weaker than the Kd for apoptotic cell membranes.

The dissociation constants were obtained in the following way. A stock solution of NBD analogue was diluted in TES buffer (5 mM TES, 145 mM NaCl, pH 7.4) to a final concentration of 1 μM in a 5 mL cuvette. With stirring, aliquots of 10 mM phospholipid vesicles of the appropriate composition were sequentially added to the solution to give the desired phospholipid concentration over the range 0 to 100 μM. After each addition, the fluorescence intensity was measured after a twenty-second incubation. Curves of fluorescence intensity ($\lambda_{530}$) versus available phospholipid concentration (taken as 60% of the total phospholipid concentration) were generated and fitted to a 1:1 binding model. An iterative curve-fitting method yielded the apparent dissociation constants.

Example 11

Figure 12:
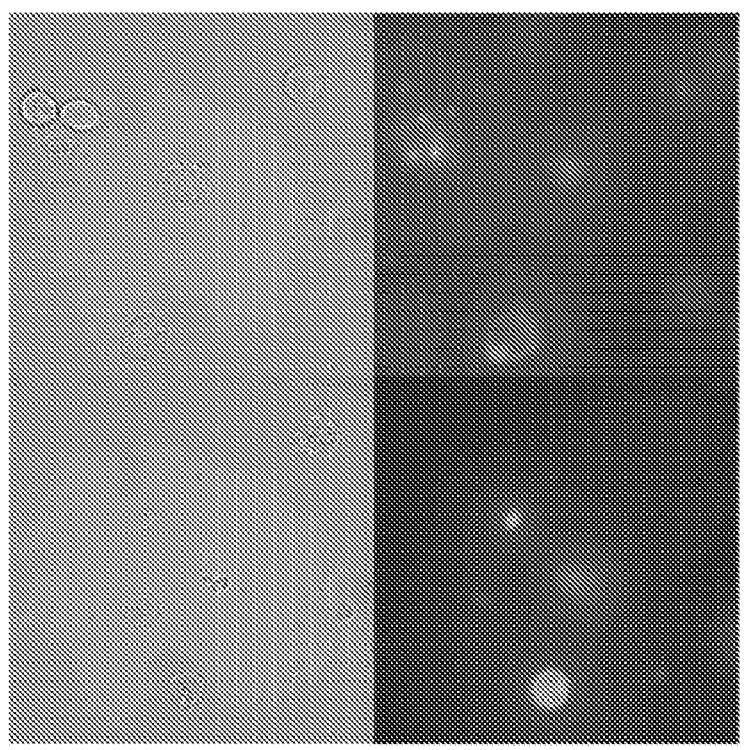
FIG. 12 presents phase contrast (left) and fluorescence (right) images of apoptotic Jurkat cells due to treatment with camptothecin and subsequently staining with PSS-794.

Fluorescence Microscopy Imaging of Apoptotic Cells with PSS-794: Jurkat cells were cultured in RPMI 1640, 10% FCS and incubated at 37° C., 5% $CO_2$. Aliquots of cells were treated with camptothecin (10 μM final concentration) in growth media for 3.5 h at 37° C., 5% $CO_2$. Cells were then treated with PSS-794 at the indicated concentrations. The cell suspensions were mixed thoroughly by repeated inversion and then incubated 15 min at 37° C. Cells were then centrifuged at 2500 rpm for 2 minutes, re-suspended and washed three times in phenol-free RPMI 1640, 10% FCS growth media. At this point, 200 μL of each cell suspension was transferred to an 8-well chamber slide for microscopy. Fluorescence microscopy was performed immediately after cell staining on an Axiovert S100 TV microscope. Pictures were taken using a black and white digital camera and colored upon acquisition using Metamorph software version 6.2. FIG. 12 provides phase contrast (left) and fluorescence (right) images of apoptotic Jurkat cells due to treatment with camptothecin and subsequently staining with PSS-794.

Example 12

Fluorescence Imaging of Dying Tumor In Living Mice with PSS-794: The EMT-6 mouse mammary carcinoma cell lines are tumorigenic in nude mice and sensitive to chemotherapy with Taxol (Paclitaxel). Mice were anesthetized with a cocktail of ketamine (87 mg/kg) and xylazine (13 mg/kg) via intraperitoneal injection. About $1\times10^5$ cells were injected subcutaneously in the right shoulder of each mouse. Growth of subcutaneous tumors is easy to monitor and typically results in tumors within 7-10 days.

When tumors reached approximately 10 mm in diameter, the mice were divided into two groups: Taxol (n=6) and Untreated (n=3). Three mice from the Taxol group received an IP injection of 12 mg/kg Paclitaxel and given 24 h for the drug to take effect. Next, the mice were administered PSS-794 via the tail vein and subjected to the 24 h imaging protocol. The same experiment (n=3) was performed using a Cy7 control fluorophore. The untreated group did not receive chemotherapy, but was given PSS-794 and subjected to the imaging protocol.

Figure 13:
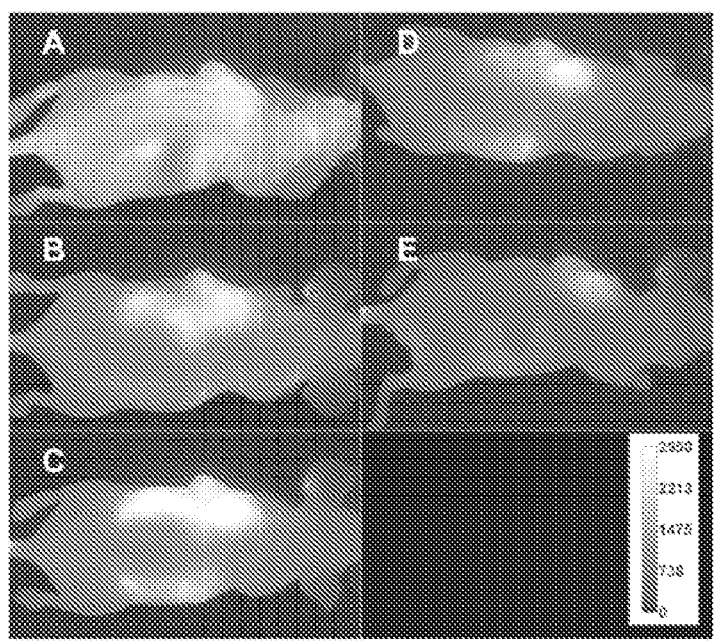
FIG. 13 presents fluorescence images of a mouse with an EMT-6 tumor on its front left shoulder. The mouse was treated with Taxol 24 h prior to intravenous injection of PSS-794. The mouse was imaged at 0 (A), 3 (B), 7 (C), 12 (D), and 24 (E) hours.

For in vivo imaging, mice were anesthetized by IP injection of a ketamine/xylazine cocktail. Molecular probe localization in the mouse tumor model is visualized by fluorescence detection (exc. 755 nm, em 830 nm) using the Kodak IS4000MM multimodal imaging system. Absorption, fluorescence and X-ray images were acquired at 0, 3, 6, 12, and 24 h post injection of PSS-794. The image acquisition time for fluorescence detection in the NIR range was 60 seconds with no binning. X-ray images were acquired for 5 seconds with maximum energy. Collected images (16-bit) were analyzed for signal strength by region of interest (ROI) using the ImageJ software suite. Fluorescence signal in the tumor region was normalized to a corresponding ROI in the contralateral limb for comparison between mice. FIG. 13 provides the resulting images.

Example 13

Figure 14:
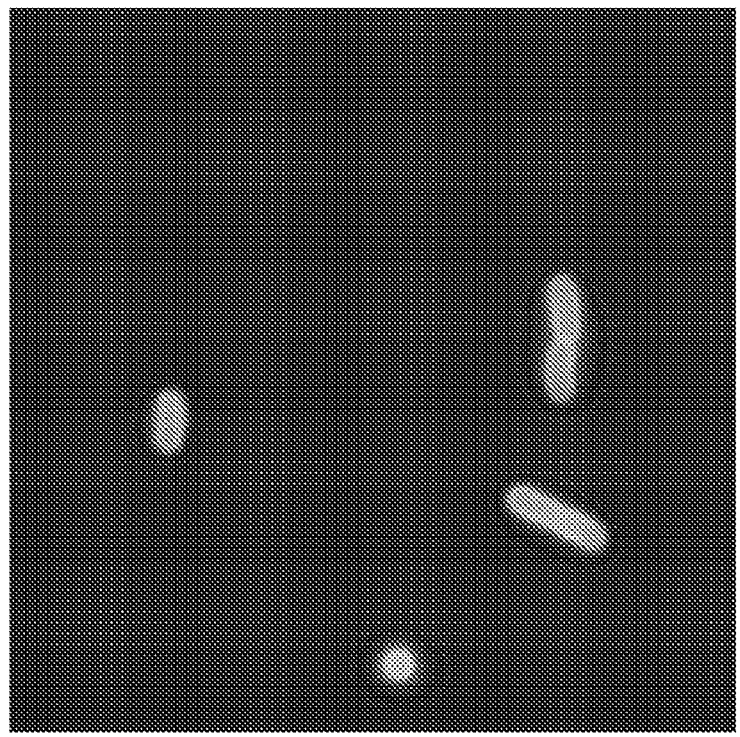
FIG. 14 presents a fluorescence image of bacterial cells that have been stained with PSS-480.

In Vitro Bacteria Imaging: After growing in media, E. coli cells ($5\times10^5$ colony forming units) were centrifuged, re-suspended in buffer, and then treated with PSS-480 (10 μM). FIG. 14 presents a fluorescence image of the bacterial cells that have been stained with PSS-480.

Example 14

Figure 15:
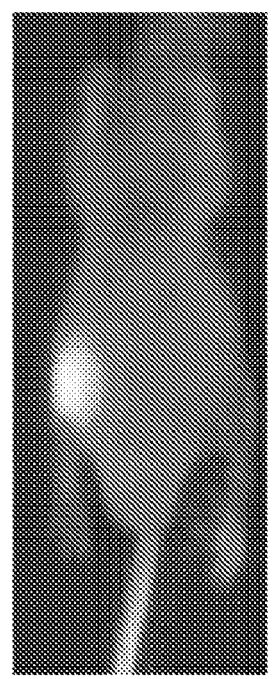
FIG. 15 presents a fluorescence image of a living mouse with a bacterial infection in its left rear thigh. The mouse was injected with a *S. aureus* NRS11 infection (~5×10$^7$ Colony Forming Units in 50 µL Luria Bertani broth) in the left rear thigh. The opposite side of the mouse was injected with only the LB vehicle as a negative control. The infection was allowed to incubate for 6 hours, followed by introduction of PSS-794 (75 µL of 1 mM aqueous stock solution) into the blood stream via a tail vein injection. The fluorescent probe clears slowly from the blood stream, except for significant accumulation at the site of bacterial infection. The fluorescence intensity from the infected muscle after 21 h was 3.7±0.6 times higher than the contralateral control muscle.

In Vivo Bacteria Imaging: Nude mice (n=4) were each injected with a S. aureus NRS11 infection (~$5\times10^7$ Colony Forming Units in 50 μL Luria Bertani broth) in the left rear thigh. The opposite side of the mouse was injected with only the LB vehicle as a negative control. The infection was allowed to incubate for 6 h, followed by introduction of PSS-794 (75 μL of 1 mM aqueous stock solution) into the blood stream via a tail vein injection. The fluorescent probe clears slowly from the blood stream, except for significant accumulation at the site of bacterial infection. FIG. 15 presents a fluorescence image of one mouse with a bacterial infection in its left rear thigh. The fluorescence intensity from the infected muscle after 21 h was 3.7±0.6 times higher than the contralateral control muscle.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:
1. A compound for detecting the presence of an anionic cell surface element, said compound consisting of the following structure:
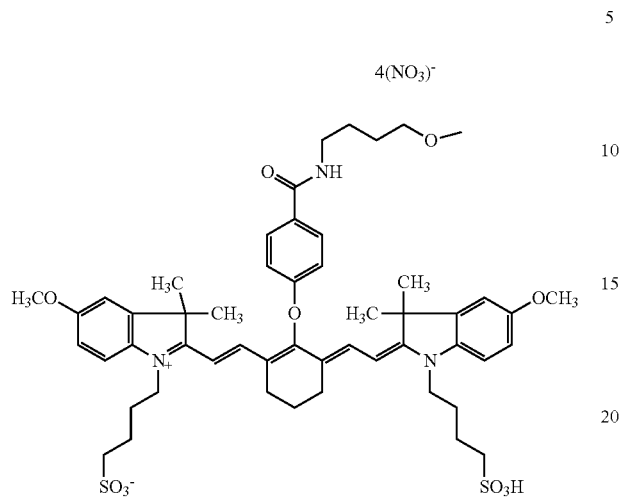
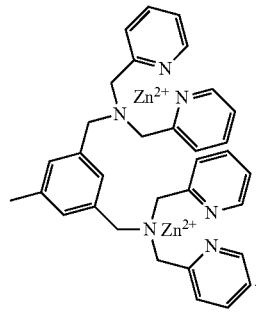
2. A compound for detecting the presence of an anionic cell surface element, said compound consisting of the following structure:
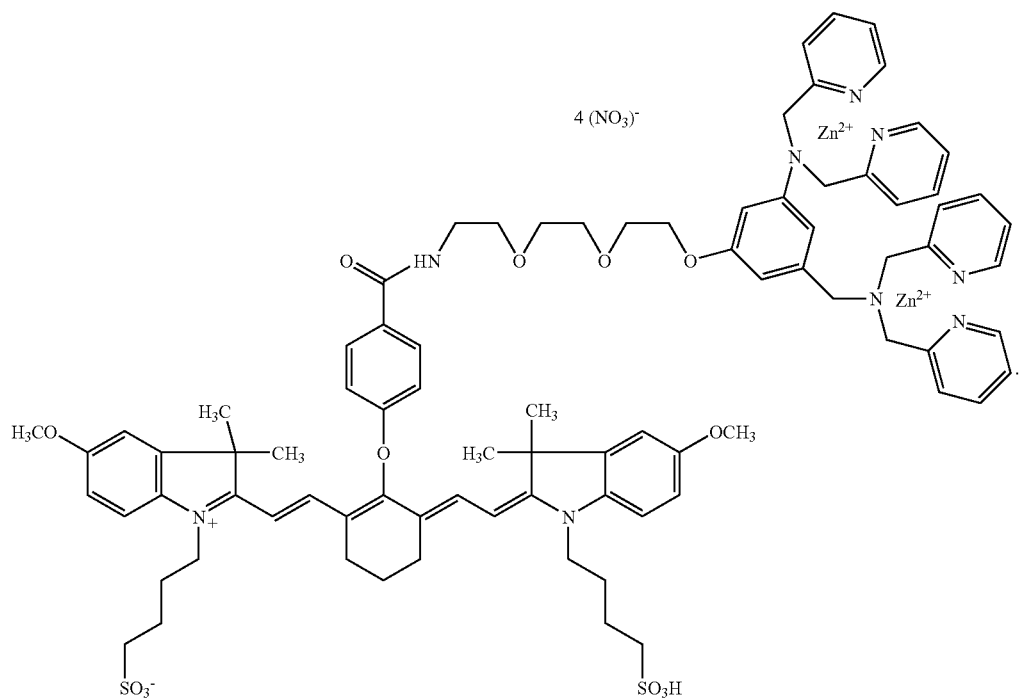
* * * * *